(12) United States Patent
Brewitt

(10) Patent No.: US 6,239,105 B1
(45) Date of Patent: *May 29, 2001

(54) HOMEOPATHIC PREPARATIONS OF PURIFIED GROWTH HORMONE

(75) Inventor: Barbara A. Brewitt, 5557 36th Ave. NE., Seattle, WA (US) 98107

(73) Assignee: Barbara A. Brewitt, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/251,820

(22) Filed: Feb. 17, 1999

Related U.S. Application Data

(63) Continuation-in-part of application No. 08/855,096, filed on May 13, 1997, now Pat. No. 6,024,734, which is a continuation-in-part of application No. 08/710,040, filed on Sep. 10, 1996, now Pat. No. 5,629,286, which is a continuation of application No. 08/488,722, filed on Jun. 8, 1995, now abandoned, which is a continuation-in-part of application No. 08/221,365, filed on Mar. 31, 1994, now abandoned.

(51) Int. Cl.$^7$ .................................................. A61K 38/27
(52) U.S. Cl. ........................... 514/12; 530/303; 530/350; 514/2; 514/12; 424/520; 424/551; 424/578
(58) Field of Search ................................. 514/12; 424/520, 424/551, 578; 530/350, 303

(56) References Cited

U.S. PATENT DOCUMENTS

| | | | |
|---|---|---|---|
| 5,114,722 | * | 5/1992 | Zoubek et al. ......................... 424/520 |
| 5,427,800 | * | 6/1995 | Cingotti ................................. 424/489 |
| 5,597,797 | * | 1/1997 | Clark ........................................ 514/12 |
| 5,629,286 | * | 5/1997 | Brewitt ...................................... 514/2 |
| 6,024,734 | * | 2/2000 | Brewitt .................................. 604/500 |

OTHER PUBLICATIONS

Goodman & Gilman's The Pharamacological Basis of Therapeutics, 9th ed., pp. 1364–1367, 1996.*

Vasgerau "Early Research and Recent Results in Therapy With Potency Accord" Biochemical Therapy, vol. X, No. 1, pp. 197–208, 1992.*

Fougery, S., et al, Affect of High Dilutions of Epidermal Growth Factor (EGF) on In Vivo Proliferation of Keratinocyte and Fibroblast Cell Lines, *British Homeopathic Journal* V.82, No. 2, p. 124–125, 1993.

Boericke, Oscar E. A.B., M.D., "Homoeopathic Materia Medica," 9$^{th}$ Ed., Boericke & Tafel, Inc., Santa Rosa CA (1927).

Dolisos Laboratories, "Nomenclature Homeopathizue Dolisos—Product Catalog," p. 103 (1991).

Smith, Rudolph B., Jr., et al., "Modern Instrumentation for the Evaluation of Homeopathic Drug Structure," *Journal of the American Institute of Homeopathy*, pp. 263–279 (Sep.–Oct., 1966).

Benveniste, Jacques, "Transfer of Biological Activity by Electromagnetic Fields," *The Center for Frontier Sciences*, vol. 3, No. 2, pp. 13–15 (Fall, 1993).

Kleijnen, Jos et al., "Clinical Trials of Homoeopathy," *The British Medical Journal*, vol. 32, pp. 316–323 (Feb. 9, 1991).

Linde, Klaus et al., "Are the clinical effects of homoeopathy placebo effects? A meta–analysis of placebo–controlled trials," *The Lancet*, vol. 350, pp. 834–843 (Sep. 20, 1997).

Rudman, Daniel MD, "Growth Hormone, Body Composition, and Aging," *Journal of American Geriatrics Society*, vol. 33, No. 11, pp, 800–807 (Nov. 1985).

Corpas, Emiliano et al., "Growth Hormone (GH)—Releasing Hormone—(1–29) Twice Daily Reverses the Decreased GH and Insulin–Like Growth Factor–I Levels in Old Men," *Journal of Clinical Endocrinology and Metabolism*, vol. 75, No. 2, pp. 530–535 (1992).

Ho, Ky et al., "Diagnosis of Growth Hormone Deficiency in Adults," *Endocrinology and Metabolism*, vol. 1 (Suppl. A) pp. 61–63 (1994).

Iranmanesh, Ali et al., "Age and Relative Adiposity are Specific Negative Determinants of the Frequency and Amplitude of Growth Hormone (GH) Secretory Bursts and the Half–Life of Endogenous GH in Healthy Men," *Journal of Clinical Endocrinology and Metabolism*, vol. 73, No. 5, pp. 1081–1088 (1991).

* cited by examiner

Primary Examiner—F. T. Moezie
(74) Attorney, Agent, or Firm—Ann W. Speckman

(57) ABSTRACT

The present invention comprises homeopathic preparations of purified growth hormone, as well as methods and systems for delivery of such preparations and treatment of disorders and conditions by administering such preparations.

19 Claims, 16 Drawing Sheets

Double Blind Placebo-Controlled Studies of Chewable Homeopathic GH on Healthy Adults Boulder-Crossover study ■ 6C + 100C + 200C (n=13)
▲ Placebo (n=26)    ○ 6X + 12C (n=15)
● Exercise Only Without Crossover (n=3)

♦ 6X Only (n=16)
● Placebo (n=45/10)
■ 6C only (n=19)

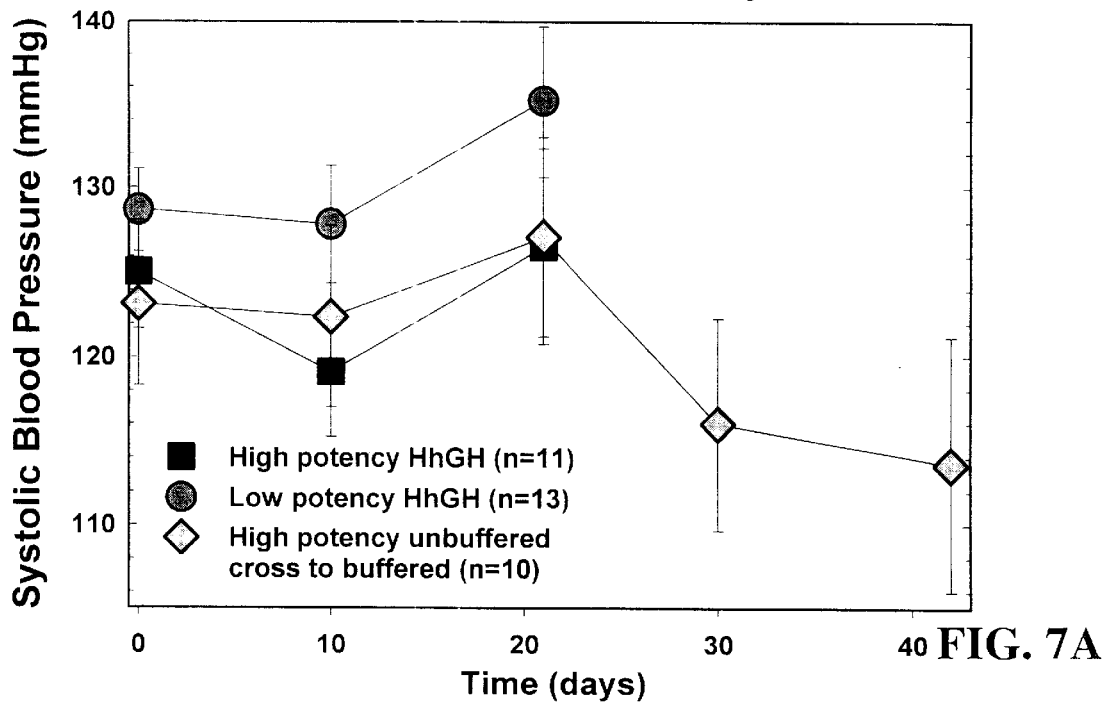
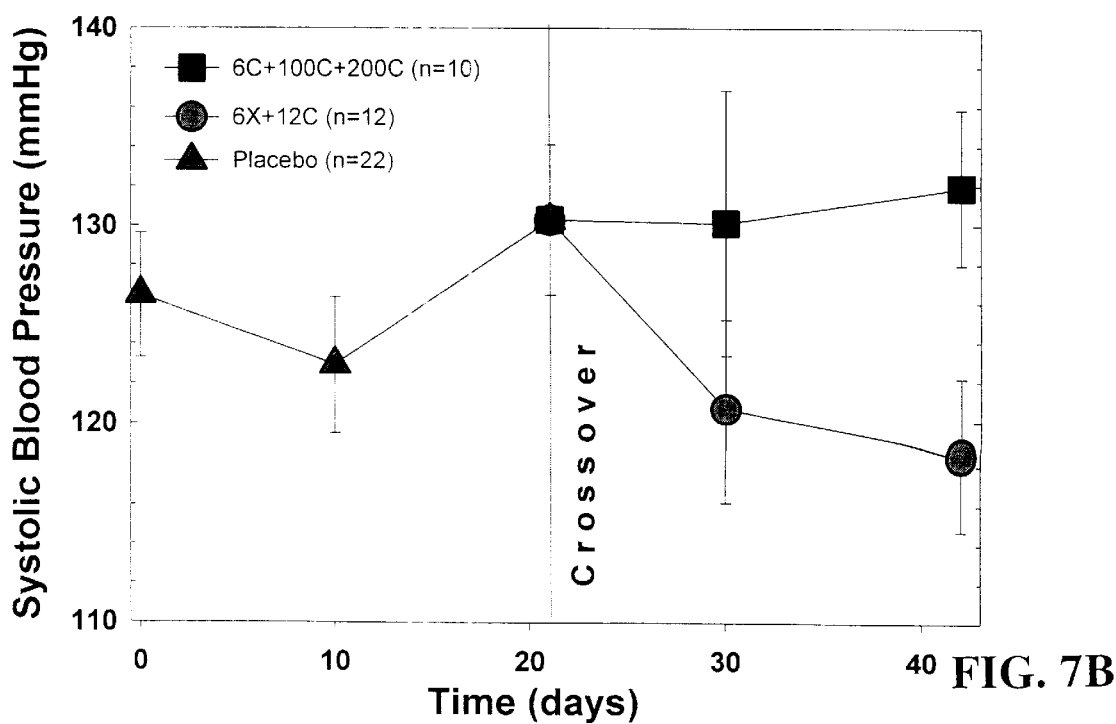

Double-Blind, Placebo-Controlled, Cross-Over Study
of Chewable Homeopathic hGH on Healthy Adults

HOMEOPATHIC PREPARATIONS OF PURIFIED GROWTH HORMONE

CROSS-REFERENCE TO RELATED APPLICATIONS

This application is a continuation-in-part of prior U.S. patent application Ser. No. 08/855,096 filed May 13, 1997, now U.S. Pat. No. 6,024,734 which is a continuation-in-part of prior U.S. patent application Ser. No. 08/710,040 filed Sep. 10, 1996, issued May 13, 1997 as U.S. Pat. No. 5,629,286, which is a continuation of U.S. patent application Ser. No. 08/488,722, filed Jun. 8, 1995, now abandoned, which is a continuation-in-part of U.S. patent application Ser. No. 08/221,365 filed Mar. 31, 1994, now abandoned. U.S. patent application Ser. No. 08/855,096, filed May 13, 1997 and U.S. Pat. No. 5,629,286 are incorporated herein by reference in their entireties.

FIELD OF THE INVENTION

This invention relates to homeopathic preparations comprising purified growth hormone, as well as methods and systems for delivery of such preparations and treatment of disorders and conditions by administering such preparations.

BACKGROUND OF THE INVENTION

Hormones and polypeptide growth factors are important regulatory substances that are involved in the regulation of cell growth and differentiation, as well as in the control of specific metabolic processes. Hormones are defined as chemical messengers that are synthesized in the endocrine glands and secreted into extracellular body fluids. Hormones are transported to hormone-responsive cells, where they bind to a hormone receptor, and the hormone-receptor complex regulates and modulates differentiated functions. Polypeptide growth factors are produced and secreted by cells from a variety of tissues, and are generally involved in paracrine and autocrine responses. Growth factors are involved in cell survival and play a crucial role in the control mechanisms governing the development and maintenance of organs and tissues. In addition to their growth promoting and differentiation inducing effects, growth factors are also involved in important physiological processes such as inflammation, immune reactions, and tissue repair.

Specific hemopoietic growth factors have been used to treat diseases such as AIDS and cancer. Hemopoietic growth factors are logical therapeutic immunomodulators to use for treatment of chronic viral infections and other diseases for several reasons. Endogenous growth factors such as granulocyte-macrophage colony stimulating factor (GM-CSF) and macrophage colony stimulating factor (M-CSF) stimulate proliferation of hemopoietic progenitor cells. Lymphocytes, macrophages and natural killer cells that normally produce these factors are quantitatively and qualitatively defective after infection by HIV, HH6V or EBV. Primates infused with GM-CSF showed low toxicity with some positive but inconsistent rises in platelet number.

Clinical studies on AIDS patients using the growth factors GM-CSF and M-CSF at pharmacological concentrations (ug/kg/day) have produced mixed results. For example, injections or intravenous administration of GM-CSF at concentrations of 0.5–0.8 ug/kg/day transiently increased leukocyte, neutrophil, eosinophil and monocyte counts in AIDS patients with no significant rise in platelet counts or change in reticulocyte and lymphocyte counts (Miles, S. 1992 AIDS Res. Hum. Retrovirises 8:1073–1080). Subcutaneous injections of 0.25–4.0 ug/kg/day improved leukocyte counts with no improvement in hemoglobin or platelet counts. However, the side effects included increased HIV replication, increased levels of P24 antigen, chills, nausea, myalgia and flu-like symptoms (Poli, G. et al. 1991 J. Exp. Med. 173:589–597; Scadden, D. T. 1990 Hematopoietic Growth Factors in Trans. Med., Wiley-Liss Inc., New York, pp. 163–176). GM-CSF also occasionally caused thrombocytopenia. Granulocyte colony stimulating factor (G-CSF) has been effective in correcting neutropenia with some minor increases in lymphocyte counts. Additionally, hemoglobin and reticulocytes increased in numbers in patients given G-CSF alone or in combination with erythropoietin. However, resumption of treatment with AZT after use of these growth factors led to severe anemia. Pharmacological doses of growth factors often have harsh side effects.

Following puberty, there is an exponential decline in growth hormone (Rudman, D,, 1985, J. A. Ger. Soc., 33:800–807). By thirty years of age, the normal physiological concentration found in the blood stream is 20 ng/ml (Corpas, E., Harman, S., Pineyro, M., Robertson, R., Blackman, M., 1992, J. Clin. Endocrinol. Metab., 75:530–535). This is reduced to 10 ng/ml by age 60, and continues to decline 2–4 ng/ml each decade (Irranmanesh, A., Lisarraide, G., Veldhuis, J., 1991, J. Clin. Endocrinol. Metab., 73:1081–1088). Additional studies have shown that growth hormone secretion peaks at approximately 31 years of age and then continues to decline by 14 to 50% per decade, dependent on gender, activity level and diet, or with the onset of chronic disease (Ho, K., Veldhuis, J., Endocrinol. Metab., 1994 1 (Suppl A):61–63). While the definition of GH deficiency is not absolute, symptoms associated with age-related declines in hGH are often used to define GH deficiency. The American Association of Clinical Endocrinology and the American College of Endocrinology suggest that growth hormone deficiency is characteristically defined as a cluster of self perceived symptoms which include fatigue, decreased lean body mass, decreased muscle mass, abdominal obesity, reduced cardiac performance, poor sense of well being, poor sleep and decreased physical strength.

Growth hormone has been isolated and purified from mammalian sources and has been produced recombinantly. Administration of pharmacological dosages of growth hormone are best known for the treatment of growth hormone deficiency disorder in children. Other pharmaceutical indications for growth hormone include: reducing blood pressure and improving cardiovascular function; increasing serum IGF-1 levels; treating growth deficiency disorders; increasing lean body mass, muscle mass and physical strength; improving pulmonary function, vascular and intracellular nutrient support; revitalizing liver, spleen, and brain functions; increasing libido and sex hormones; improving lipoprotein balance and fatty acid levels; increasing energy levels, oxygen uptake, nitrogen retention, physical mobility and exercise performance; eliminating cellulite and improving cholesterol profile; promoting hair growth; improving dermal cellularity and collagenicity; increasing cartilage strength; increasing the size and function of the thymus and spleen; enhancing immune system function and lymphocyte count; and reducing body fat. Pharmacological application of growth hormone has been shown to improve short term memory; reduce the sense of social isolation; improve REM sleep quality, improve vision, remove wrinkles, quicken wound healing, and generally contribute to a feeling of well-being. Additionally, homeopathic preparations of the present invention may be used to treat AIDS wasting syndrome, Turner syndrome, osteoporosis, Parkinson's, and Alzheimer's disease.

Administration of higher than physiological concentrations of growth hormone does, however, produce serious side effects, including tissue turgor, neuropathy, back pain, increase in liver enzymes aspartate aminotransferase (SGOT) and alanine aminotransferase SPGT, increased sweating, headache, skin and joint problems, hypertension, and edema. It would thus be desirable to identify compositions or means of administration that, when administered, produce the benefits of growth hormone without producing the serious side effects.

Homeopathy, which dates back to the nineteenth century, is founded on the principles of pharmacology and biology. In 1877, Hugo Schultz postulated that the effect of a stimulus on a living cell is indirect and proportional to its intensity and quantity. Later, in 1888, Schultz demonstrated that very low concentrations of yeast toxins increased yeast growth over 100 fold. Concurrently, the psychiatrist Rudolph Arndt developed his "Basic Law of Biology," which states that weak stimuli slightly accelerate the vital activity, middle-strong stimuli raise it, strong stimuli suppresses it, and very strong stimuli halt vital activity. These separate observations were formulated by Arndt in 1888 into one of the earliest laws of pharmacology representing the homeopathic effect, the Arndt-Schultz law, which states: every stimulus on a living cell elicits an activity, which is inversely proportional to the intensity of the stimulus (Martius F. Das Arndt-Schultz Gnindgesetz, Muench Med. Wschr., 1923, 70(31):1005–1006). This law was later restated by Hueppe as: for every substance, small doses stimulate, moderate doses inhibit, large doses kill. Allopathic medicine, with its emphasis on moderate drug doses, works to inhibit undesired physical symptoms and to kill undesired pathogens. Homeopathic medicine begins with small doses and moves towards higher and higher dilutions to stimulate the body's own natural electromagnetic forces.

Homeopathic and allopathic principles can be represented on the same sinusoidal curve (shown in FIG. 1). There are several harmonic concentrations over a log scale of dilutions that give the same desired effect. Oscillatory data demonstrating the stimulating and inhibiting effect of log dilutions of anti-IgE antisera which caused human basophil degranulation have been generated and reproduced (Davenas, E., Beauvais, F. et al. *Nature* 333:816–818, 1988; Beneviste, J., Davenas, E. et al. *C. R. Acad. Sci. Paris* 312, series II, pp. 461–466, 1991). Control studies using dilutions of antihuman IgG antisera or simply distilled water did not produce this same effect.

This phenomena of oscillatory or polyphasic activity is further described by Bellavite, P. and Signorini, A., in Homeopathy: A Frontier in Medical Science, North Atlantic Press, Berkeley Calif., 1995 at page 130. The essential constituents of homeostatic biological systems susceptible to polyphasic activity based on concentration of drug or growth factor have the following characteristics: Firstly, that there be adjustable and reversible effector functions, such as occurs in the endocrine gland. Secondly, that there be signal molecules that enable nearby and remote structures to communicate via feedback systems, such as neurotransmitters, hormones, local chemical mediators and cytokines/growth factors. A particular feature of the signal molecules is that their message is never wholly specific; the same molecules can be used to communicate between different physiological systems. There is a substantial degree of redundancy of biological information, which enables complex biological systems a considerable measure of flexibility. This inherent complexity makes it difficult to develop a rigid schematization of the events following the production of a certain mediator in given pathophysiological conditions. Thirdly, that there be cell surface receptors involved, which are capable of increasing, by hypersensing or priming, or decreasing, by desensitization, tolerance, adaptation or downregulation, the number of receptors according to their needs. Additionally, the cell surface receptors are capable of regulating activity by modifying the affinity for the signal molecules. On occasion, the cells present more than one receptor for the same molecule, but with different affinities and intracellular effects. Lastly, that the multiform characteristics of the signal transduction systems have a level of responsiveness that is also controlled by such systems in the cell, and that they are also modified in the course of disease and are highly susceptible to concentration-specific modulation.

One of the basic tenets of homeopathic medicine is that a cure for a disease can be evoked by using a high dilution medicine that resembles but is different from the cause of the disease. Homeopathy is widely accepted as a useful therapeutic throughout Europe, the British Commonwealth countries and India, and has been demonstrated to have characteristic and reproducible effects. A critical review of more than 100 controlled and/or clinical studies of homeopathy determined that patients received positive healing benefits from homeopathy beyond the placebo effect (Kleijnen, J. et al. 1991 Brit. Med. J. 302:316–323; Linde, K., Clausius, N., Ramirez, G., Melchart, D., Eitel, F., Hedges, L. V., Jonas, W. B., 1997, Lancet, 350:834–843; Reilly, D., et al, 1994, Lancet, 344:1601–1608).

Many homeopathic medicines are used at concentrations of micrograms ($10^{-6}$ M) and nanograms ($10^{-12}$ M); however, in other homeopathic preparations, the dilutions exceed Avogadro's number ($6.023 \times 10^{-23}$). When homeopathic compounds are diluted 1:10, with repeated succusions (similar to vortexing) and repetitively diluted by this procedure at least 24 times, a potency is achieved ($10^{-24}$) that is so highly dilute that the probability of a single molecule of the original substance remaining in the volume used is less than $1 \times 10^{-10}$. Homeopathic practitioners believe that the potency of a compound increases with increasing dilutions. In traditional homeopathic practice, the standard homeopathic dosage is 10–15 drops of a $10^{-12}$ molar, or 6 C, solution administered two to three times per day. A $10^{-60}$ molar or 30 C may be given one to three time per day. A $10^{-400}$ molar or 200 C may be given only one time per month or year. A 6 C dilution approximates 1 picogram/ml, which is used in cell culture but would be considered a lower than physiological dose when administered to a patient either orally, topically or by injection.

Highly dilute homeopathic medicines have been effective in treating some conditions, including viral infections, in vivo. Homeopathic dilutions of $1 \times 10^{-200}$ to $1 \times 10^{-1000}$ of typhoidinum, hydrophobinum, tuberculinum, nux vomica and malandrinum 100% inhibited pock-like lesions caused by a chicken embryo DNA virus on the chorio-allantoic membrane compared to controls (Singh, L. M. and Gupta, G. 1985 Brit. Homeopathy 74:168–174). Other homeopathic medicines, the same medicines at different homeopathic concentrations, or control phosphate buffered solution (PBS), had lesser or no effect.

While the exact mechanism of action of homeopathic medicines is unknown, magnetic resonance image measurements on serial dilutions of substances indicate that the hydroxyl (OH) groups in the solvent of solutions continue to change as dilutions become successively higher (Sacks, A. D. 1983 J. Holistic Med. 5:175–176; Smith, R. and Boericke, G. 1968 J. Am. Inst. Homeopathy 61:197–212;

Smith, R. and Boericke, G. 1966 J. Am. Inst. Homeopathy 59:263–279). It is clear that the specific effects of homeopathics are of a non-molecular origin, yet provide potent biological activities that are clinically effective. It has been postulated that highly dilute compounds transfer biological activity to cells by electromagnetic fields (Benveniste, J. 1993 Frontier Perspectives 3:13–15). Del Giudice et al. have hypothesized that interactions between the electric dipoles of water and the radiation fields of a charged molecule generate a permanent polarization of water which becomes coherent and has the ability to transmit specific information to cell receptors, somewhat like a laser (Del Giudice, E., Preparata, G., Vitiello, G. 1988, Phys. Rev. Lett. 61:1085–1088).

Certain hormones have been prepared and used homeopathically. Adrenalinum, or ephinephrine, a sympathomimetic hormone produced by the medulla of the adrenal glands, thyroidinum, a preparation from the thyroid gland, and adrenocorticotrophin, or cortocotropin, a polypeptide hormone that increases the rate of secretion of the adrenal corticosteroids, are included in the official Homeopathic Monographs from the General Pharmacy of the Homeopathic Pharmacoepia of the United States. Insulin, an active molecule found in the pancreas which affects sugar metabolism, is listed in Boericke's Materia Medica, and is noted for its applicability for skin conditions. Parathyroid hormone, an extract from the parathyroid gland; thyreotrophic hormone, an extract from the anterior lobe of the pituitary gland; Corticotrophin, also extracted from the anterior lobe of the pituitary gland; cortisone and corticoids, which are steroid hormones; and folliculinum, a hormone secreted by the ovaries, are listed in the Materia Medica of New Homeopathic Remedies by Julian. The clinical symptomatology for parathyroid hormone includes general weakness, depression, asthenia, hypotonia, fatigue, pallor and emaciation. The clinical symptomatology for thyreotrophic hormone include various conditions of the mind, digestive system, circulatory system, respiratory system, sense organs, and urinary and genital organs. The clinical symptomatology for corticotrophin include various psychological and nervous conditions. The symptomatology of cortisone and corticoids includes various psychological, nervous, endocrine and digestive system conditions. The clinical symptomatology for folliculinum includes various conditions of the mind, digestive system and circulatory system.

A common principle of homeopathy is the Law of Similars, which was founded in the science of pharmacology and states that a drug has two effects on the body, a direct effect and the subsequent reaction of the body to the drug, evoking symptoms or side effects. In homeopathy, as the drug is diluted, some of the positive benefits of the drug remain, plus new characteristics of the drug become available to the body which not only alleviate side effects, but have new characteristic features that actually ameliorate other symptoms the person may have.

SUMMARY OF THE INVENTION

Growth hormone, or somatotropin, is a well-characterized single chain alpha-helical polypeptide containing a discrete receptor binding domain. Human growth hormone is the most abundant hormone secreted by the anterior pituitary gland and has significant anabolic and anti-catabolic effects on the body. Cells of the immune system, such as macrophages and lymphocytes also produce and secrete growth hormone. Growth hormone stimulates the liver to produce somatomedins which, in turn, promote bone, muscle, cartilage, kidney, liver and skin growth. Two cleaved forms of human growth hormone have been isolated, one has prolactin-like activity and the other has growth promoting activity greater than that of the uncleaved molecule.

The present invention provides a homeopathic preparation comprising purified growth hormone that may be administered orally, nasally, topically or by injection and is effective in reducing blood pressure and improving cardiovascular function; increasing serim IGF-1 levels; treating growth deficiency disorders; increasing lean body mass, muscle mass and physical strength; improving pulmonary function, vascular and intracellular nutrient support; revitalizing liver, spleen, and brain functions; increasing libido and sex hormones; improving lipoprotein balance and fatty acid levels; increasing energy levels, oxygen uptake, nitrogen retention, physical mobility and exercise performance; reducing joint, back and knee pain; reducing joint swelling; eliminating cellulite and improving cholesterol profile; promoting hair growth and color change; reducing bleeding of the gums, nasal and sinus congestion; improving dermal cellularity and collagenicity; increasing cartilage strength; increasing the size an function of the thymus and spleen; enhancing immune system function and lymphocyte count; and reducing fat, in particular, hip and waist size. Homeopathic preparations of the present invention furthermore may be used to improve short term memory; reduce the manifestations of anger, anxiety, depression, social isolation, mood swings and sleeping disorders, improve vision, remove wrinkles, quicken wound healing, breast enlargement, and generally contribute to a feeling of well-being. Additionally, homeopathic preparations of the present invention may be used to treat headaches, AIDS wasting syndrome, Turner syndrome, osteoporosis, Parkinson's, and Alzheimer's disease.

Homeopathic preparations of the present invention are non-toxic and do not produce undesirable side effects. They can be formulated and provided to a large patient population at a reasonable cost by means of delivery systems that are convenient and safe. Homeopathic preparations of the present invention are preferably administered via oral or topical delivery systems, or using eye drops, nasal or throat sprays, transdermal delivery, or other routes of administration that do not involve injection and that do not require sterile equipment or the participation of health care professionals. Alternatively, the present invention may also be administered by means of intracutaneous, intramuscular, intravenous, or subcutaneous injection.

The homeopathic preparations of the present invention preferably comprise one or more potencies of purified growth hormone at a concentration, or homeopathic potency, of less than about $10^{-6}$ molar, and preferably between about $10^{-6}$ molar and about $10^{-100,000}$ molar. Some of the homeopathic preparations may thus contain few or no molecules of growth hormone. Homeopathic preparations of the present invention are defined as comprising purified growth hormone if the preparation is derived from or originated from a preparation comprising a measurable quantity or activity of purified growth hormone, preferably, the recombinant human growth hormone having a bioactivity of about 2.6 Units/mg based on World Health Organization (WHO) reference standard.

Preparations of growth hormone according to the present invention may contain multiple potencies of purified growth hormone and/or other purified constituents, such as purified growth factors, etc., in addition to the growth hormone. Homeopathic preparations comprising one or more of the following potencies of purified growth hormone are preferred: 6 X ($10^{-6}$ M); 6 C ($10^{-12}$ M); 12 C ($10^{-24}$ M); 30 C ($10^{-60}$ M); 100 C ($10^{-200}$ M); 200 C ($10^{-400}$ M); and 1M=1,000 C ($10^{-2000}$ M). Especially preferred homeopathic preparations of the present invention comprise multiple potencies of purified growth hormone, including 6 X and 12 C potencies, as well as a combination of 6 C with 100 C and 200 C potencies. Various potencies of growth hormone may be combined with other purified constituents, such as growth factors, vitamins, minerals, amino acids, and/or traditional homeopathics, the purified constituents having a potency greater than or equal to 3 X ($10^{-3}$ M). In particular, combinations of one or more growth factors at various potencies is preferred, including granulocyte macrophage-colony stimulating factor (GM-CSF), granulocyte-colony stimulating factor (G-CSF), macrophage-colony stimulating factor (M-CSF), tumor necrosis factor (TNF-α), insulin-like growth factor (IGF), transforming growth factor-β (TGF-β), nerve growth factor (NGF), epidermal growth factor (EGF), stem cell factor (SCF), platelet-derived growth factor (PDGF), fibroblast growth factors (FGF), interleukin-1, interleukin-2, keratinocyte growth factor, ciliary neurotrophic growth factor, insulin, Schwann cell-derived growth factor, vaccinia virus growth factor, bombyxin, neu differentiation factor, v-Sis, glial growth factor/acetylcholine receptor-inducing activity and other proteins belonging to their structural superfamilies. Examples of traditional homeopathics that may be used in combination with homeopathic preparations of growth hormone include arsenicum, pulsatilla, aconite, hypericum and metabolic sarcodes. The same potencies, or combinations of potencies, of homeopathic preparations of purified growth hormone and additional constituents are used regardless of whether the administration is in liquid, solid, spray, topical, transdermal or injectable form.

Homeopathic preparations comprising a purified growth hormone are preferably administered orally, in liquid or solid form, such as pellets or tablets. Oral administration is convenient and effective. Alternative delivery systems, such as eye drops, nasal sprays, throat sprays, topical preparations, transdermal delivery, injectables (intracutaneous, intramuscular, intravenous, or subcutaneous), systems also provide convenient and effective delivery of the homeopathic preparations comprising growth hormone. Oral delivery of polypeptides and proteins is generally ineffective, since the polypeptides and proteins are generally broken down and rendered inactive in the blood stream before they reach their desired target or exert their desired effect. Traditionally, polypeptides and proteins are thought to be effective only when delivered via injection, intranasally or intravenously, and undesirably high dosages are administered because a large proportion of the delivered dosage is destroyed prior to exerting its effect or reaching its target. The mechanism of action of the homeopathic preparations of the present invention comprising a purified growth hormone has not been fully delineated, but is generally thought to exert its effects in a non-molecular nature. It is postulated that homeopathic preparations transfer biological activity to cells by electromagnetic fields. Although the mechanism is undefined, the clinical effects of such preparations, delivered orally using liquid or chewable tablet formulations, have been demonstrated in numerous patients, and demonstrated in a double-blind, placebo controlled study, as described below.

Purified growth hormone for use in homeopathic preparations of the present invention may be isolated from natural sources, or it may be produced using recombinant techniques or other polypeptide synthesis technology. Growth hormone isolated from mammalian sources, or produced recombinantly to have substantially the same structure and activity as human growth hormone, is preferred. The purity of the growth hormone used in homeopathic preparations of the present invention is preferably at least about 90%, and more preferably at least 95%. Human growth hormone is preferred, although growth hormone polypeptides that are different from but have a high degree of similarity to human growth hormone molecules are suitable. Purified recombinant human growth hormone (rhGH) is commercially available from several sources, including NovoNordisk Eli Lilly, Pharmacia/Upjohn, Ares Serono and Genentech. In addition to overall purity, the biological specific activity of recombinant human growth hormone is approximately 2.6 Units/mg based on World Health Organization (WHO) reference standard.

Analysis of human growth hormone have characterized important functional epitopes for binding to its native receptor, human growth hormone binding protein (hGHbp). Approximately 31 side chains of hGH participate in the receptor-ligand interaction, but only eight of these side chains account for 85% of binding energy (Clackson, T. & Wells, J. S., A hot spot of binding energy in a hormone-receptor interface, Science 1995, 267:383–386). Therefore it is preferable that the recombinant human growth hormone used in homeopathic preparations possess this functional epitope in a biologically active form. Additional components, such as stabilizers, buffers, preservative compounds, etc. may be used and are well known in the art, as described in the United States Homeopathic Pharmacopoeia.

DESCRIPTION OF THE FIGURES

FIGS. 2–12 provide graphical illustrations of the results of three double blind, placebo-controlled cross-over studies of healthy adults described, below, in Example 1. More specifically.

FIG. 7A shows the effect of treatment using a 6 X+12 C potency, a 6 C+100 C+200 C potency and an unbuffered 6 C+100 C+200 C potency crossed-over to a buffered 6 C+100 C+200 C potency homeopathic preparation of recombinant human growth hormone on systolic blood pressure, and FIG. 7B shows the effect of treatment using a 6 X+12 C potency and a 6 C+100 C+200 C potency homeopathic preparation of recombinant human growth hormone on systolic blood pressure;

DETAILED DESCRIPTION

Figure 1:
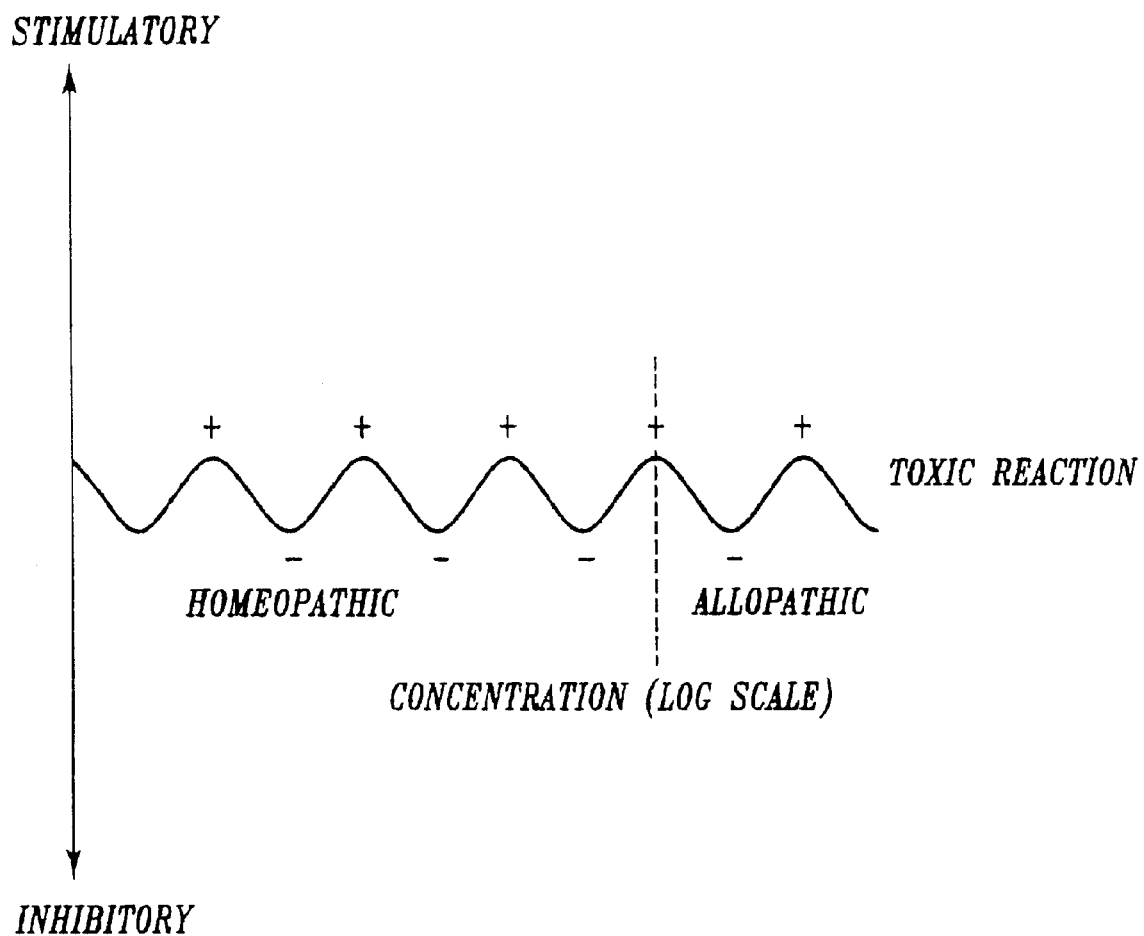
FIG. 1 illustrates the relationship between the concentration of a substance and the stimulating and inhibiting effects of homeopathic and allopathic medicines. The repeating sinusoidal relationship demonstrates that different concentrations of a substance over a very broad range of concentrations can be stimulatory or inhibitory.

The homeopathic preparations of the present invention typically comprise between $1 \times 10^{-6}$ and $1 \times 10^{-100,000}$ molar concentrations of purified growth hormone in a pharmaceutically acceptable diluent. Homeopathic preparations preferably comprise a concentration of $1 \times 10^{-6}$ M purified growth hormone or less and, alternatively or additionally, comprise a concentration of $1 \times 10^{-12}$ M purified growth hormone or less, preferably a concentration of $1 \times 10^{-24}$ M purified growth hormone or less, and most preferably comprise a concentration of $1 \times 10^{-60}$ M purified growth hormone or less. Homeopathic preparations of the present invention preferably comprise a homeopathic potency of purified growth hormone of one or more of the following potencies: 6 X; 6 C; 12 C, 30 C, 100 C and 200 C.

Various diluents or substrates may be used, depending on the desired delivery system. Appropriate diluents for the following delivery systems are well known: oral administration in liquid or solid form; eye drops; nasal sprays; throat sprays; injectables; topical preparations; and transdermal preparations. One or more potencies of purified growth hormone and/or one or more additional constituents, such as a purified growth factor, vitamins, minerals, amino acids, or traditional homeopathic preparations, may be combined in a preparation. The preferred homeopathic diluents for oral administration are a solution of purified water, glycerin, citric acid and a preservative such as sodium benzoate; or a solution of purified water, glycerin, potassium sorbate, and/ or a form of proteinated-copper in a cationic state, and a preservative such as sodium benzoate. Other diluents for oral delivery, including various alcohol-containing solutions, are known in the art and may be employed in the present invention to increase solubility and stability of purified growth hormone. The homeopathic preparations of the present invention are preferably administered orally, but may also be prepared in topical formulations for application to the skin; administered transdermally; by intracutaneous, intramuscular, intravenous, or subcutaneous injection; or administered in the form of eye drops or nasal and throat sprays. Lotions for topical and transdermal application, and buffered salt solutions for eye applications, are well characterized and widely used in the cosmetic industry, which are readily adaptable to the preparation of the present invention. Additionally, carrier solutions for intranasal administration of substances are well known in the art and widely used in drug delivery systems.

In a preferred embodiment, homeopathic preparations of purified growth hormone are prepared in a chewable tablet form. The tablets are made from a suitable organic material, such as lactose (Dolisos, Las Vegas, Nev.), or sucrose by methods well known in homeopathy, as described in the United States Homeopathic Pharmacopoeia. In particular, tablets are generally produced in two forms, as tablet triturates or compressed tablets. Tablet triturates are produced by preparing a homeopathic preparation of purified growth hormone, as previously described, and adding binders as necessary. Binding solutions are composed of a binder, such as gum arabic, microcrystalline cellulose, a preservative if necessary, an inert lubricant, and purified water. The tablets are then molded by hand or preferably by automated equipment, and the tablets are then dried by introducing them into a dehumidified environment with a relative humidity of 35–40%, and an ambient temperature of 70 to 110° F. Compressed tablets are formed by compression of a dry material and contain no special coating. They are compressed from powdered or crystalline solids, and, as with tablet triturates, may contain binders, excipients, lubricants, and disintegrators. Compressed tablets are produced by adding the homeopathic preparation of purified growth hormone to the lactose preparation until thoroughly moistened. Binders may be added at this time as necessary, as described above for tablet triturates. The moistened material is granulated by passing through an appropriate mesh screen, and the moistened granulation is introduced into a dehumidified environment and subsequently dried as described above. The dried granulation is then regranulated through the mesh screen and lubricants, such as mineral oil, talc, calcium stearate, corn starch, are added as necessary. The mixture is then compressed in a rotary tablet compressor or any similar apparatus to the desired tablet size.

EXAMPLE 1

A series of studies were conducted on healthy adult subjects to ascertain the effect of various potencies of recombinant human growth hormone ("rhGH"). Specifically, three studies evaluating a total of 162 healthy individuals ages 18–72 were conducted in some form of a double-blind, placebo controlled study (DBPCS). Individuals were excluded from the studies who reported any chronic conditions, such as AIDS, cancer, or other diseases. Also individuals reporting any use of steroids, prednisone, or injectable growth hormone were also excluded.

The first study, referred to as the Seattle Study, was a thirty day DBPCS that included 15 subjects ranging in age from 18 to 57 years who exercised regularly three to five times per week. Subjects were randomly divided into two groups: one group received a combination 6 C+100 C+200 C homeopathic hGH formulation (bovine-derived growth hormone from Sigma Co.), and the other group received placebo.

The second study, referred to as the Santa Fe Proving Study, included 46 individuals aged 19 to 59 years old who enrolled for a classical Homeopathic proving, without knowing the test substance. The Proving Study was designed in accordance with the principles of classical homeopathy where all subjects were given a placebo in bottle "A" and instructed to take one chewable tablet three times per day for seven days: one in the morning between 7:00 and 8:30 am; one in the afternoon between 3:00 and 4:00 pm; and one in the evening between 5:00 and 8:30 pm. The subjects were instructed to chew the tablet carefully and not swallow it. After seven days of treatment, there was a wash out period for an additional seven days where no substance was given. After this wash out period, subjects were given bottle "B," which contained a single potency of either 6 X or 6 C or placebo.

The third study, referred to as the Boulder Study, enrolled 87 individuals, ages 29 to 72 years old, who did not exercise regularly. This was a 42-day double-blind, placebo controlled study with crossover after 21 days to the opposite test substance, i.e., treatment regimens are switched. For example, a group initially receives placebo and after 21 days "crosses over" to receiving treatment with a homeopathic preparation. Table I describes the different groups and the treatment regimen. Specifically, test subjects received one of two formulations of homeopathic GH, a low potency 6 X+12 C (higher concentrations of hGH), or a higher potency, 6 C+100 C+200 C (lower concentration of hGH), or placebo. Both formulations and the placebo were administered by chewable tablets. After three weeks, all subjects were crossed over to either placebo or one of the two treatments, as described above. Furthermore, group 5 (refer to Table I) was administered a 6 C+100 C+200 C potency combination of HrhGH throughout the 42 day trial. Additionally, a control group consisting of three subjects who exercised regularly, ages 33, 35 and 62, were enrolled to determine whether exercise alone would increase IGF-1 levels and lean body mass (this group did not receive treatment or placebo). Each participant received instruction on the proper dosage (three times daily) and method of administration (chewable tablets) before being issued the 21-day supply of the substance. Group assignments were not revealed to the subjects or experimenters until the study was completed. Most subjects in the Seattle Study and all subjects in the Boulder Study had some knowledge of the perceived benefits of over-the-counter growth hormone related products. No one in the Santa Fe Proving Study knew the substance being tested.

TABLE I

| Group | Treatment - Days 1–20 | Cross-over Treatment - Days 21–42 |
|---|---|---|
| 1 | 6C + 100C + 200C rhGH n = 16 | placebo |
| 2 | Placebo n = 15 | 6X + 12C rhGH |
| 3 | 6X + 12C rhGH n = 15 | placebo |
| 4 | placebo n = 20 | 6C + 100C + 200C rhGH |
| 5 | 6C + 100C + 200C rhGH- n = 13 | 6C + 100C + 200C rhGH- buffered |
| 6 | No treatment-exercise only n = 3 | No treatment-exercise only |

Baseline assessments of body composition and specific laboratory measurements were made prior to the study and every 10 days until completion of the study. Final measurements were taken at the end of 42 days, after administration of the drug or placebo. Subjects completed an evaluation of self-perceived quality of life measurements before, every 10 days during, and upon completion of treatment.

In the Seattle Study, commercially available growth hormone (bovine-derived, Sigma Chemicals) was serially diluted and hand succcussed to obtain a final tablet of 6 C+100 C+200 C, or the active ingredient and hand succession was withheld and a placebo was prepared. In the Santa Fe Study, single potencies of 6 X ($10^{-6}$ M) and 6 C ($10^{-12}$ M) homeopathic recombinant human growth hormone (HrhGH) were made, plus a placebo. In the Boulder Study, two different combination formulations of HrhGH were used for oral delivery in tablet form, the 6 C+100C+200 C, referred as the "high potency combination" and the 6 X+12 C, referred to as the "low potency combination." In addition, a placebo was prepared for the Santa Fe and Boulder studies.

Body compositions of participants in terms of lean body mass (LBM) and fat mass was determined using bioelectric impedance analysis (BIA, Bioanalogics, Beaverton, Oreg.). Blood pressure was monitored every ten days as was body shape via tape measurements of the upper arm, upper chest, hips and waist. Total body weight (without shoes) and height measurements were also taken. To serve as a reference, ideal body weight was taken from standardized health charts.

In the Seattle Study, blood samples were taken to determine serum IGF-1 levels before treatment, 14 days later and at the end of the end of the 30 day protocol. Subjects voluntarily arrived at the laboratory at a consistent time of day that was most convenient for them. At the end of the trial, subjects on placebo failed to arrive for their final blood draw. In the Boulder Study, potential diurnal fluctuations were controlled for by consistently taking blood samples between 5–7 pm. In addition to IGF-1, liver enzymes gamma-glutamyl-transpeptidase (GGPT), alanine aminotransferase (SGPT), and aspartate aninotransferase (SGOT) were monitored in order to detect potential toxicity associated with administering hGH.

1.1 Effects of Homeopathic Growth Hormone on IGF-1 levels.

Figure 16:
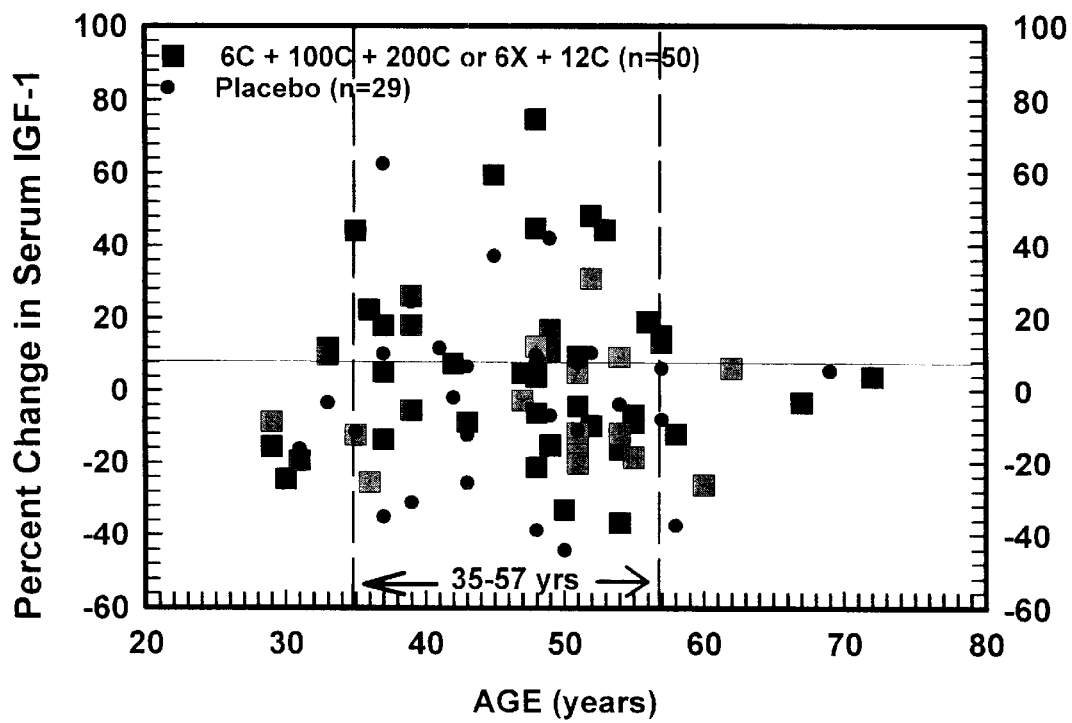
FIG. 16 represents a scatter plot of percent change in serum IGF-1 levels in relation to age in subjects after 20 days of treatment with either the 6 X+12 C potency or 6 C+100 C+200 C potency homeopathic preparation or placebo.

IGF-1 has been cited most frequently as a reliable measure of hGH physiological activity. FIG. 16 represents a scatter plot of response in subjects after 20 days of treatment or placebo. The groups receiving either the "high" or "low potency combination" of HrhGH demonstrated a 12 to 78% increase in serum IGF-1 in 28% of those subjects. In contrast only 14% of the individuals receiving placebo increased in serum IGF-1 by 12 to 62%. A common 12% increase in serum IGF-1 levels occurred in both treatment placebo groups.

Age-related changes in serum IGF-1 levels within each test group were observed. Baseline serum IGF-1 levels were generally within the normal range. In the Boulder Study, 56% of the individuals had above-average serum IGF-1 levels, however, 34% had levels below average, suggesting a potential age-related hGH deficiency in those individuals. In the groups receiving homeopathic treatments, 45–59% of individuals had serum IGF-1 baseline levels above the normal reference range compared to 67% of the individuals in the placebo group. The baseline serum IGF-1 values in the Boulder cohort ranged from 70 to 410 ng/ml. After 20 days of placebo, the range of serum IGF-1 was 52 to 382 ng/ml, demonstrating a slightly downward trend. Following 21 days of high potency combination treatment, serum IGF-1 values ranged from 103 to 494 ng/ml, demonstrating an overall upward trend, as shown in Table II.

TABLE II

| Treatment | High Potency | Low Potency | Placebo |
|---|---|---|---|
| Age (yrs.) | 50 +/− 2 | 50 +/− 2 | 46 +/− 2 |
| Age Range (yrs.) | 30–72 | 29–62 | 31–69 |
| (n) | 20 | 17 | 31 |
| IGF-1 Start | 102–274 ng/ml | 76–410 ng/ml | 70–343 ng/ml |
| IGF-1 Finish | 83–254 ng/ml | 104–374 ng/ml | 52–382 ng/ml |

FIG. 16 demonstrates that the age groups most responsive to the treatment, or a placebo effect, after 21 days of testing were 35–57 years old. Also, in the Seattle Study, subjects over 32 years old increased serum IGF-1 levels 18% (+/−5%) within the first 15 days, which then decreased to 7% (+/−10%) by 30 days. In contrast, subjects between 18 to 32 years showed no change in IGF-1 levels in the first 15 days, however this group had a 26% (+/−10%) increase in serum IGF-1 levels after 30 days of treatment.

Figure 6A:
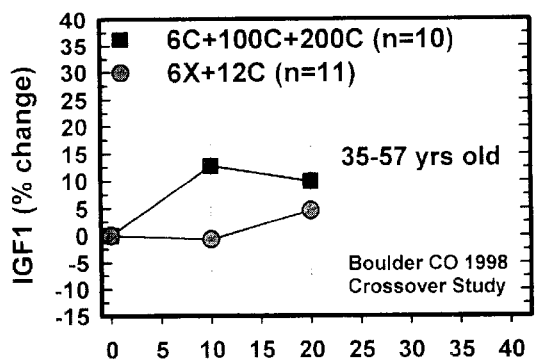
FIGS. 6A and 6B show the percentage change of $IGF_1$ levels resulting from treatment using a 6 X+12 C potency and a 6 C+100 C+200 C potency homeopathic preparation of recombinant human growth hormone.
Figure 6C:
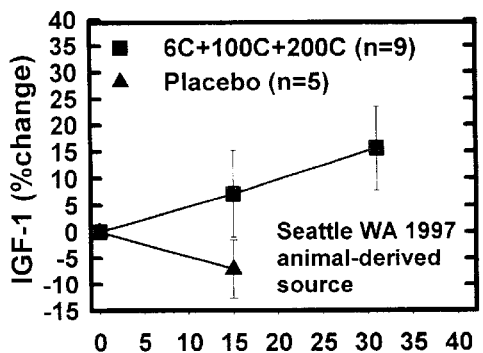
FIG. 6C shows show the percentage change of IGF, levels resulting from treatment using a 6 C+100 C+200 C potency homeopathic preparation of recombinant human growth hormone.
Figure 6B:
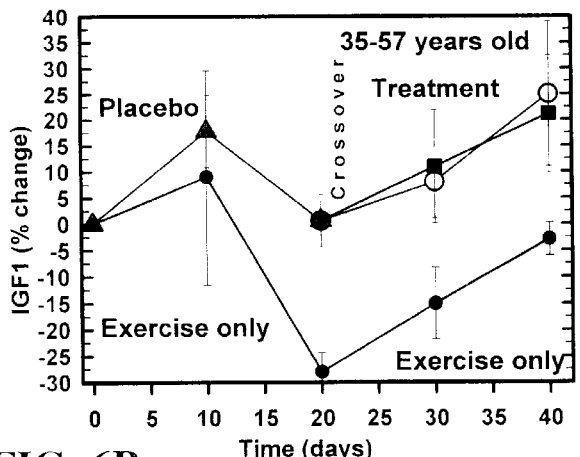
Figure 6D:
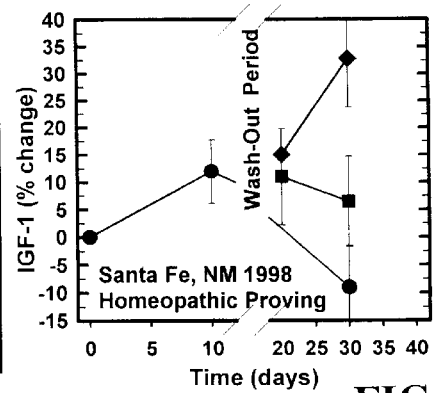
FIG. 6D shows show the percentage change of IGF, levels resulting from treatment using a 6 X potency homeopathic preparation of recombinant human growth hormone.

FIGS. 6A, B, C and D demonstrate reproducible rises in serum IGF-1 in all three studies. In the Boulder Study, the groups initially taking the low or high potency combination homeopathic formulas demonstrated a 4% (+/−12%) and 10% (+/−10%) increase in serum IGF-1 levels, respectively, after 21 days (FIG. 6A). The placebo group had no significant increase in serum IGF-1 at 21 days (−1% (+/−4%)), but did demonstrate a transient rise during the first 10 days (FIG. 6B). The control group not receiving treatment or placebo, but only exercising regularly, demonstrated a decrease of 28% (+/−4%) in serum IGF-1 levels after 21 days and ended the study at 42 days with a decrease of 3% (+/−3%). After the placebo group crossed over to treatment for 21 days, the group taking low potency combination HrhGH formulation increased in IGF-1 levels by 25% (+/−14%). Serum IGF-1 levels rose 21% (+/−13%) for the high potency combination after 21 days of treatment from the crossover point to the end of the study (FIG. 6B). FIG. 6C illustrates a 16% (+/−8%) increase in serum IGF-1 levels after 30 days of oral administration of the high potency combination formula compared to no increase (−7% (+/−6%)) with placebo after 15 days of use. FIG. 6D, from the Santa Fe Proving Study, illustrates an increase of 18% (+/−10%) in serum IGF-1 serum levels from a single 6 X potency of HrhGH after only seven days of oral administration.

1.2 Effects of Homeopathic Growth Hormone on Lean Body Mass and Total Weight.

Figure 8A:
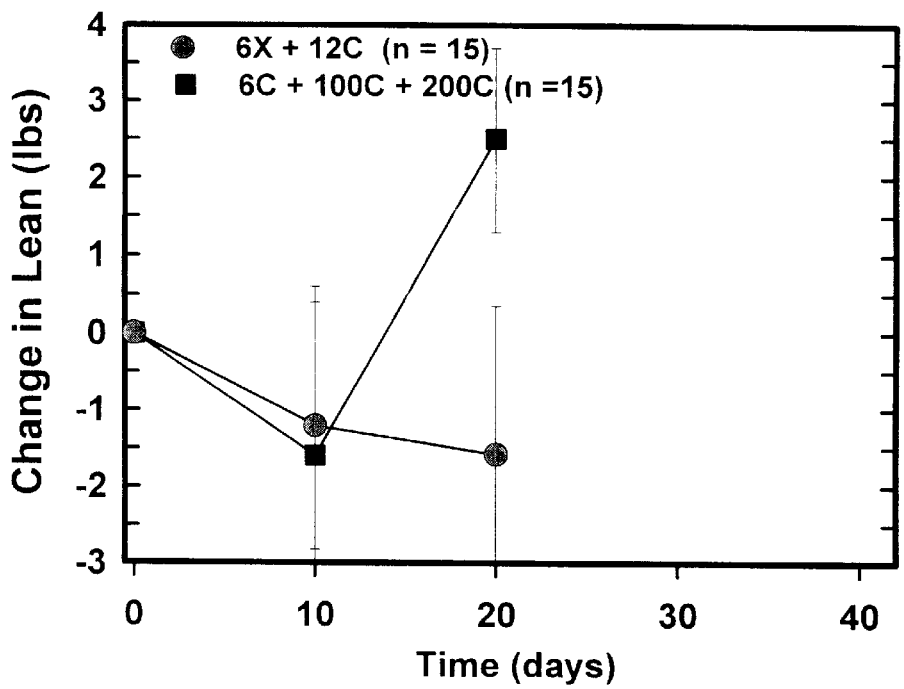
FIGS. 8A and 8B show the change in lean body mass resulting from treatment using a 6 X+12 C potency and a 6 C+100 C+200 C potency homeopathic preparation of recombinant human growth hormone.
Figure 8B:
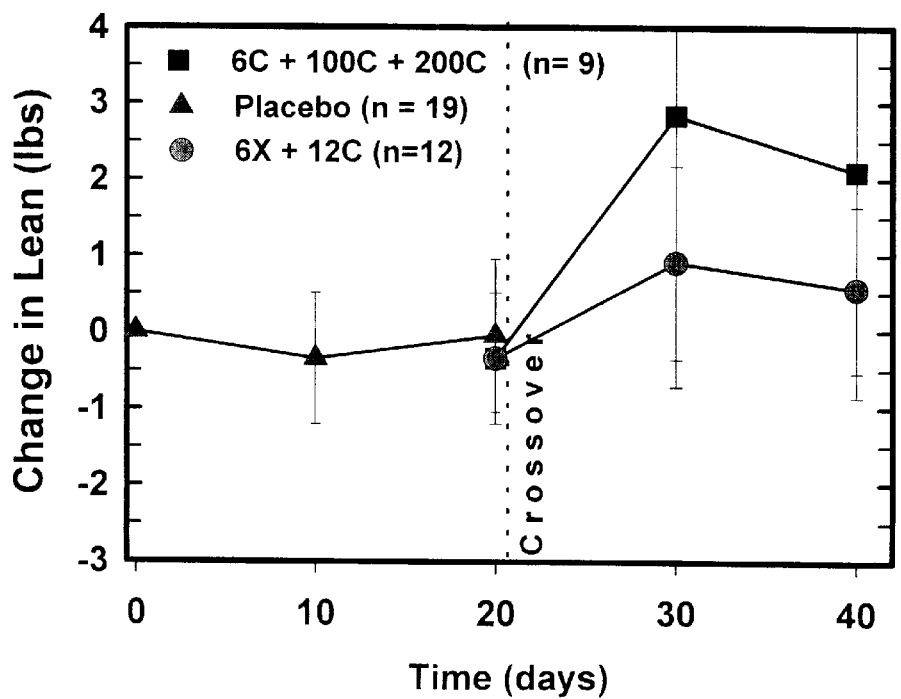
Figure 15:
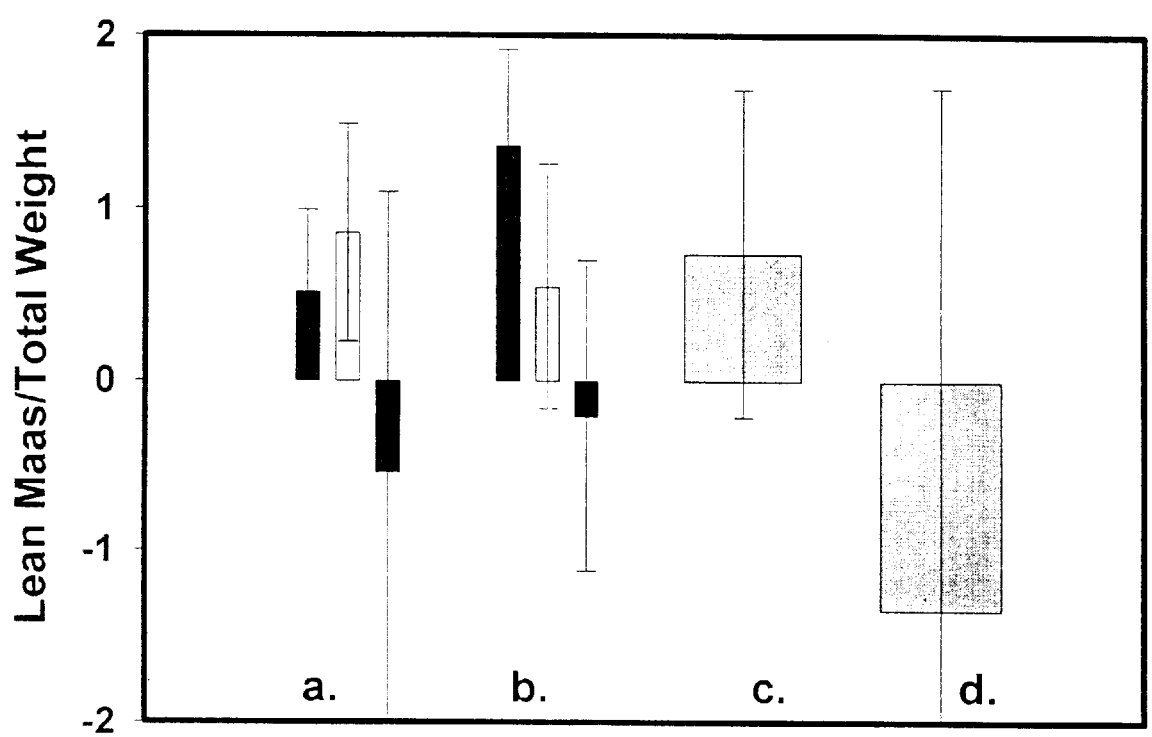
FIG. 15 shows the lean mass to total weight ratios in response to various potencies of homeopathic preparation of recombinant human growth hormone.

FIGS. 8A and 8B illustrate the change in lean body mass over time for each treatment group compared to placebo (Boulder Study). During the first 21 days on treatment with the high potency combination formula, subjects gained 2.5 lbs. (+/−1.2 lbs.) of lean body mass. These results closely approximate the total weight gained in those same groups (FIGS. 13A, 13B, 14A and 14B). In contrast, the low potency combination stimulate no net gain in lean body mass (−1.6 lbs. (+/−1.9 lbs.)) or total weight gain after the same period. The placebo group also experienced no net gain in lean body mass, 0.05 lbs. (+/−1 lbs.), yet gained 1.7 lbs. (+/−0.5 lbs.) total weight. Once the placebo group crossed over to the high potency combination formula, there was no significant lean body mass gain (2.1 lbs. (+/−3.1 lbs.)), while total weight decreased approximately −0.6 lbs. (+/−0.5 lbs.). Once the placebo group crossed over to the low potency combination formula, lean body mass increased 0.55 lbs. (+/−1.1 lbs.), while total body weight decreased 1.0 lbs. (+/−0.9 lbs.). A treatment effect occurred in terms of gain in lean body mass/total body mass. There were positive gains with both treatments at all time points compared to negative losses in lean body mass/total body mass in the placebo group or when using only exercise (FIG. 15). A positive ratio of lean mass/total mass indicates gains in lean body mass.

1.3 Effects of Homeopathic Growth Hormone on Body Dimensions.

Figure 9A:
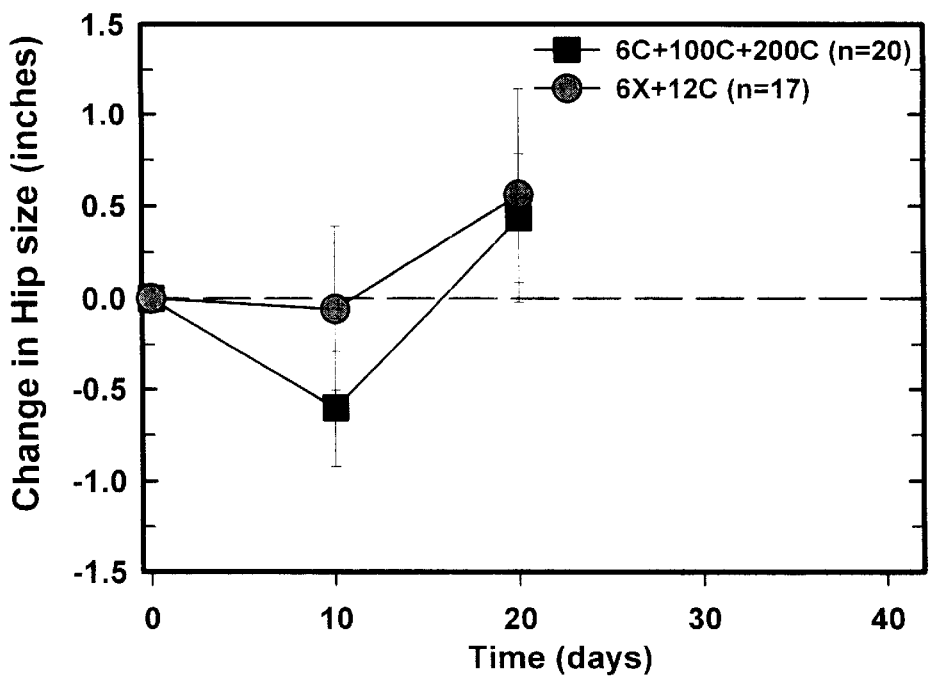
FIGS. 9A and 9B show the change in hip size resulting from treatment using a 6 X+12 C potency and a 6 C+100 C+200 C potency homeopathic preparation of recombinant human growth hormone.
Figure 9B:
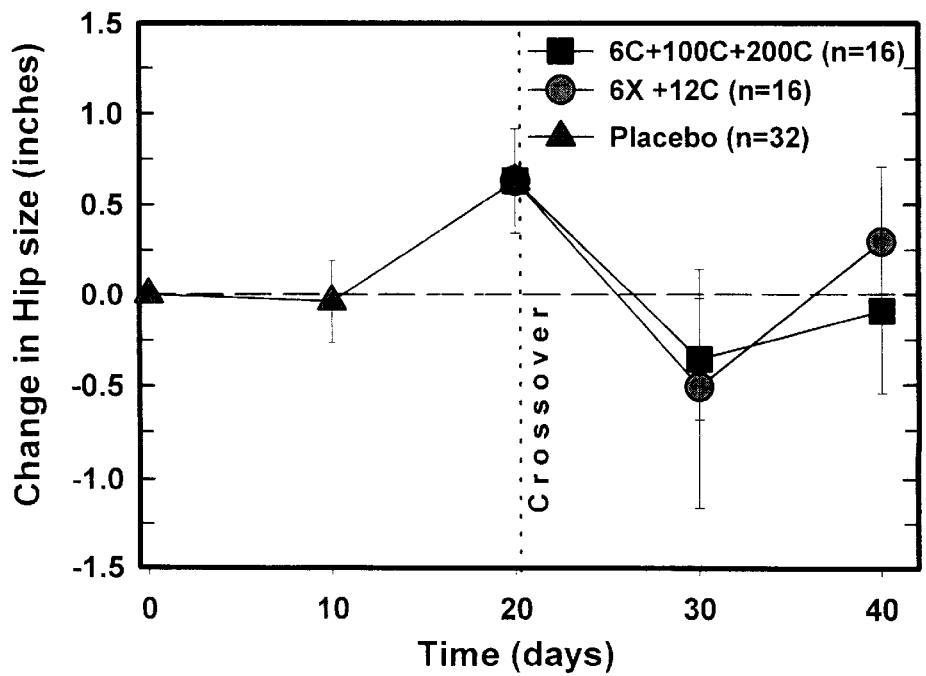
Figure 10A:
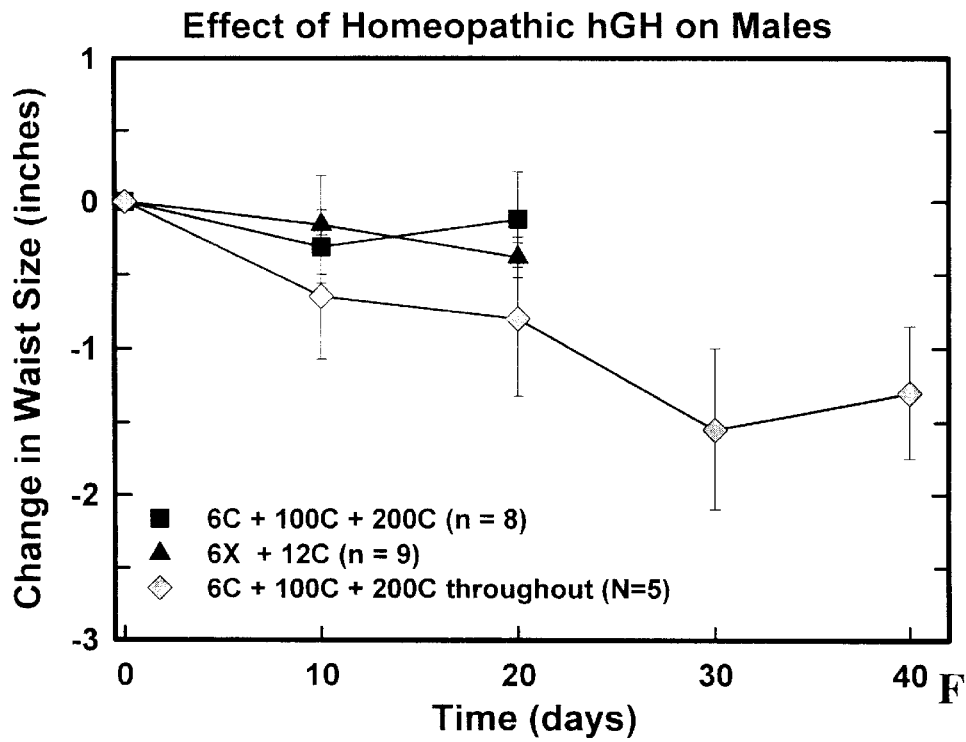
FIG. 10A shows the change in waist size in males resulting from treatment using a 6 X+12 C potency, a 6 C+100 C+200 C potency and an unbuffered 6 C+100 C+200 C potency crossed-over to a buffered 6 C+100 C+200 C potency homeopathic preparation of recombinant human growth hormone.
Figure 10B:
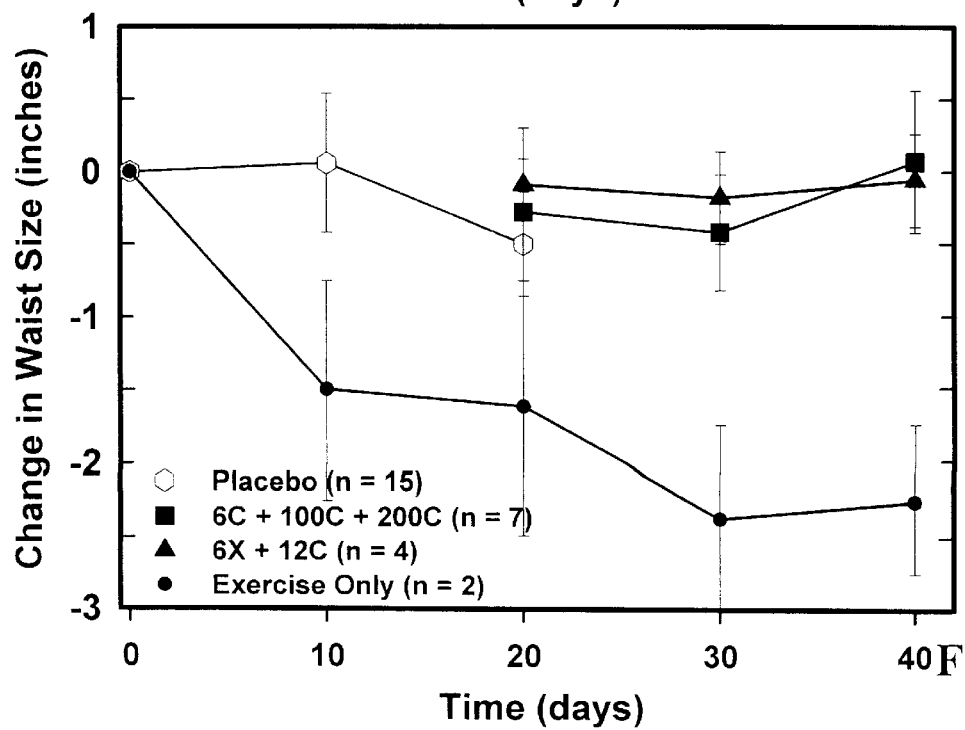
FIG. 10B shows the change in waist size in males resulting from treatment using a 6 X+12 C potency and a 6 C+100 C+200 C potency homeopathic preparation of recombinant human growth hormone.
Figure 11A:
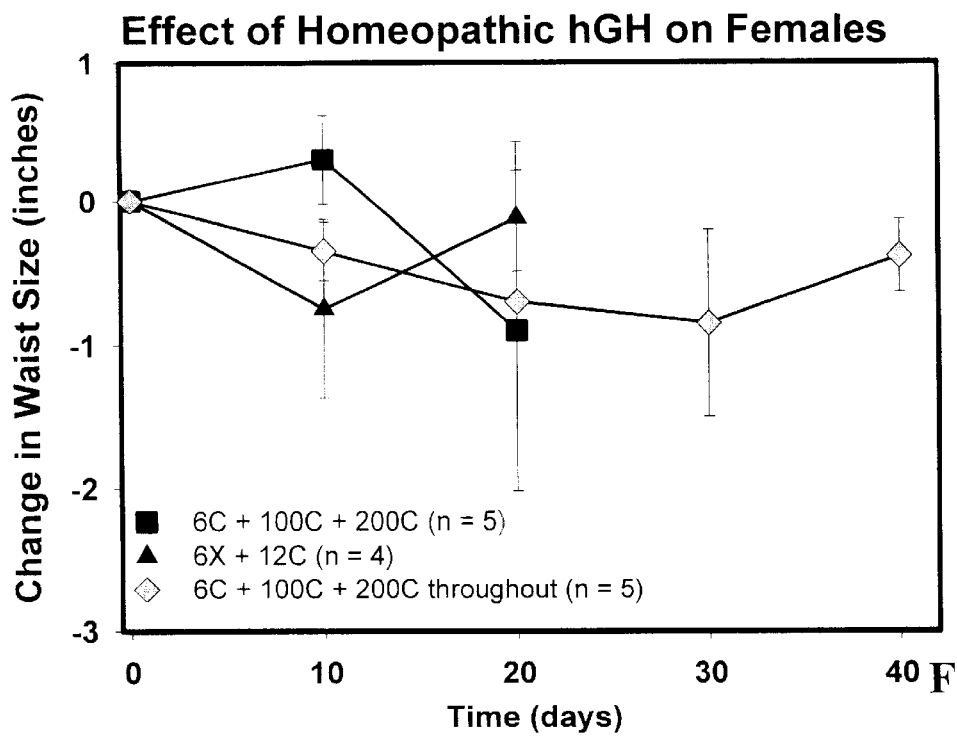
FIG. 11A shows the change in waist size in females resulting from treatment using a 6 X+12 C potency, a 6 C+100 C+200 C potency and an unbuffered 6 C+100 C+200 C potency crossed-over to a buffered 6 C+100 C+200 C potency homeopathic preparation of recombinant human growth hormone.
Figure 11B:
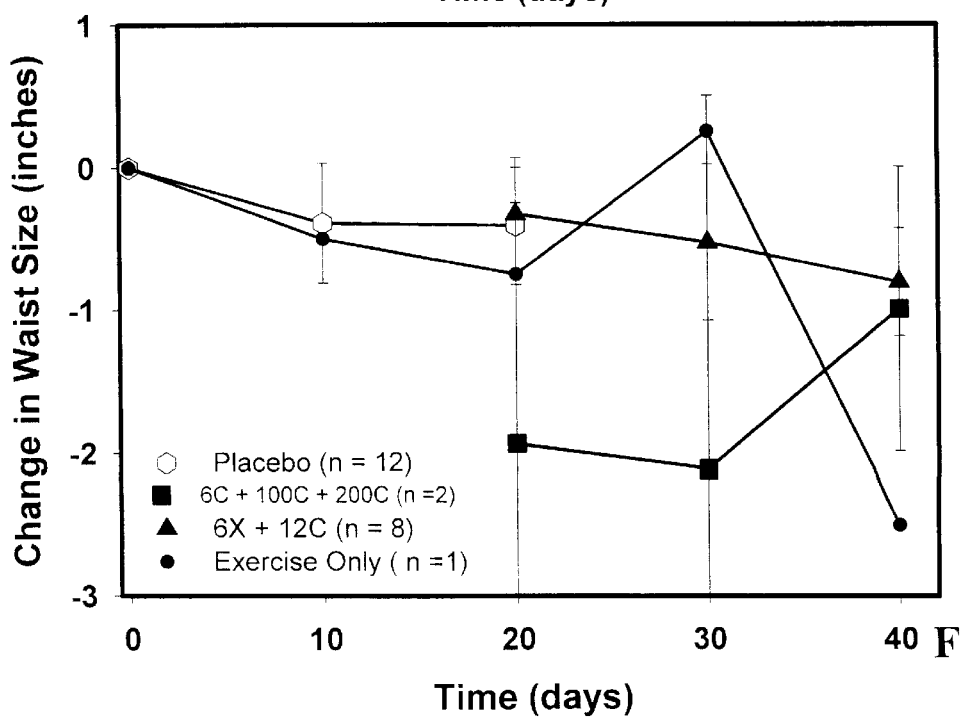
FIG. 11B shows the change in waist size in females resulting from treatment using a 6 X+12 C potency and a 6 C+100 C+200 C potency homeopathic preparation of recombinant human growth hormone.
Figure 12A:
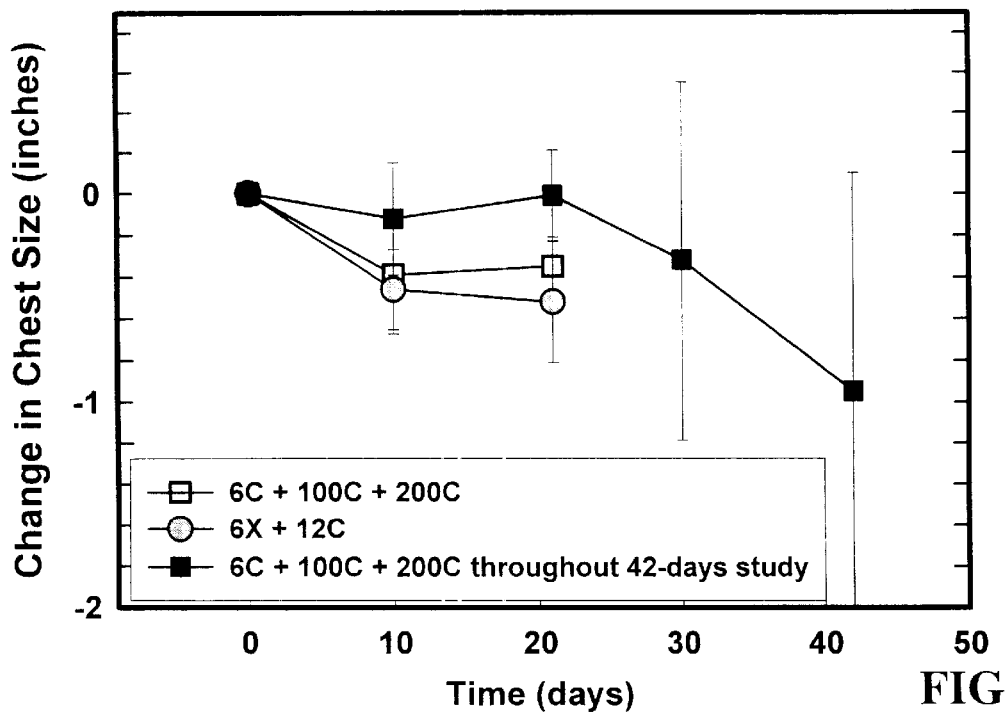
FIG. 12A shows the change in chest size resulting from treatment using a 6 X+12 C potency, a 6 C+100 C+200 C potency and an unbuffered 6 C+100 C+200 C potency crossed-over to a buffered 6 C+100 C+200 C potency homeopathic preparation of recombinant human growth hormone.
Figure 12B:
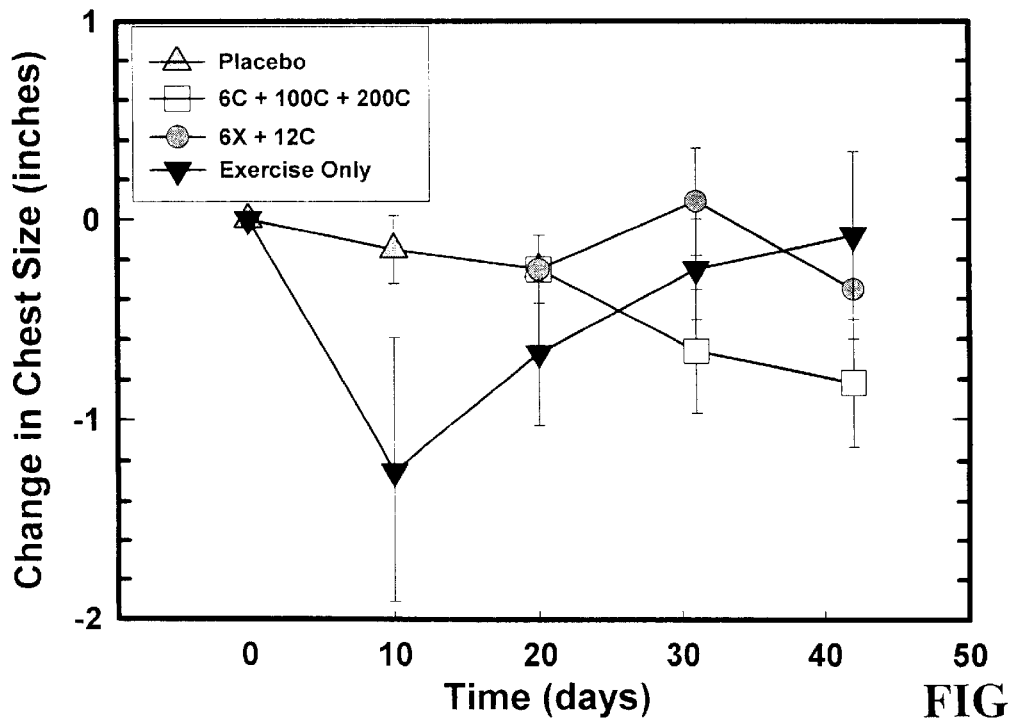
FIG. 12B shows the change in chest size resulting from treatment using a 6 X+12 C potency and a 6 C+100 C+200 C potency homeopathic preparation of recombinant human growth hormone.
Figure 13A:
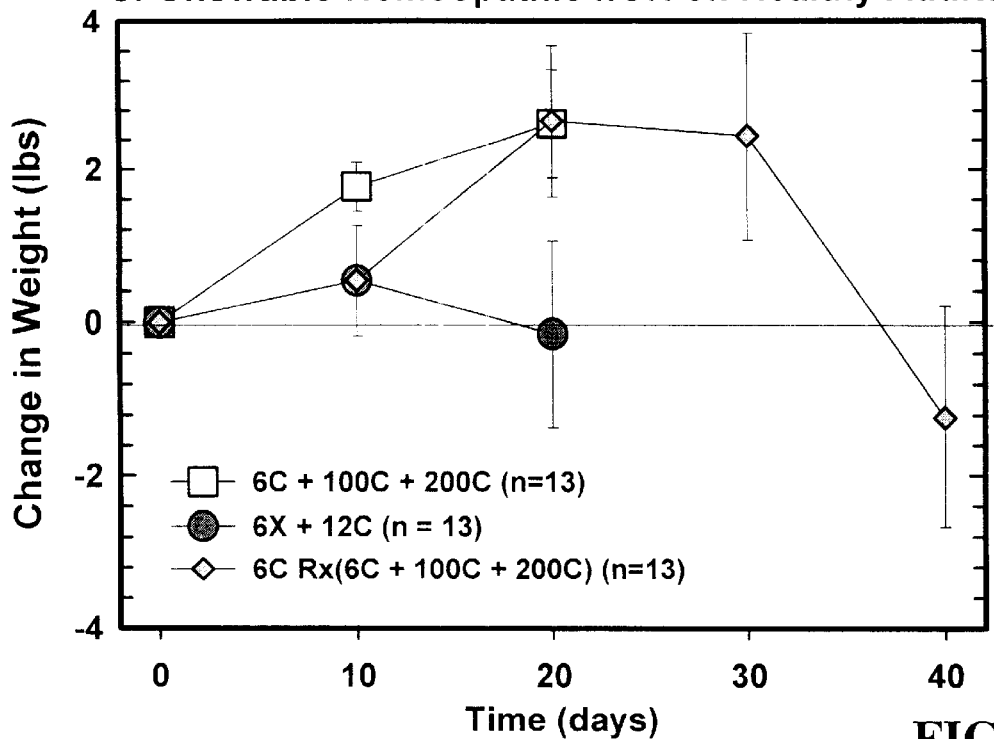
FIG. 13A shows the change in weight resulting from treatment using a 6 X+12 C potency, a 6 C+100 C+200 C potency and an unbuffered 6 C+100 C+200 C potency crossed-over to a buffered 6 C+100 C+200 C potency homeopathic preparation of recombinant human growth hormone.
Figure 13B:
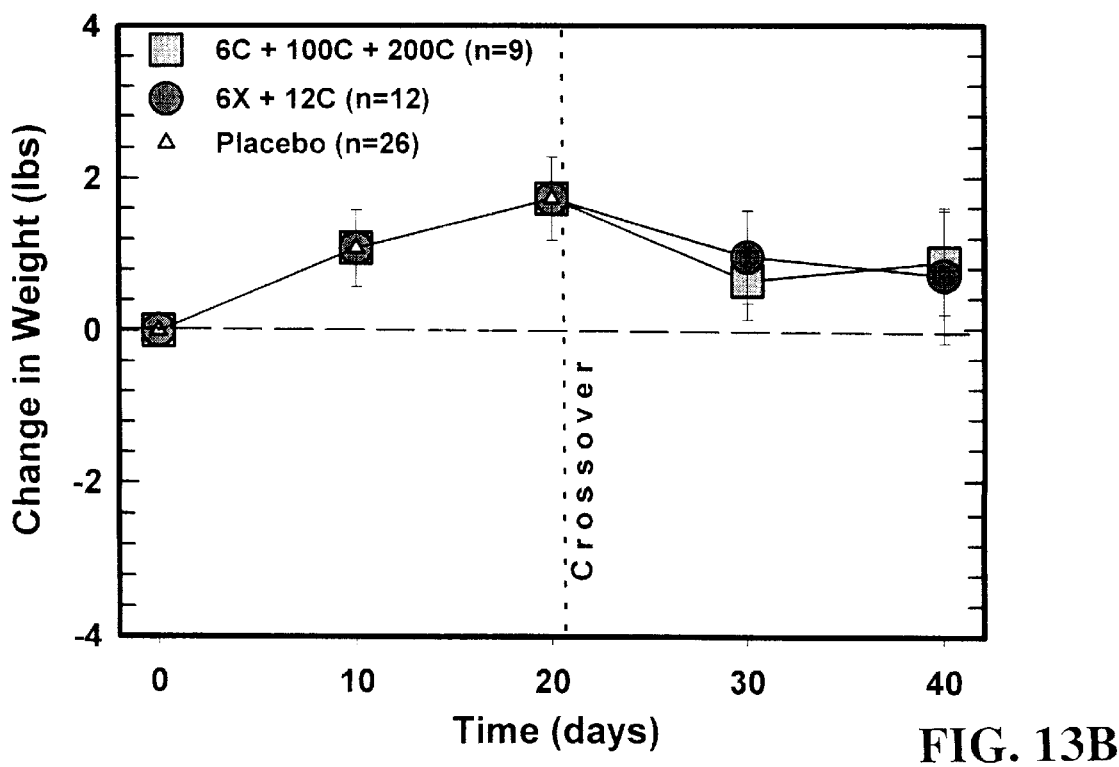
FIG. 13B shows the change in weight resulting from treatment using a 6 X+12 C potency and a 6 C+100 C+200 C potency homeopathic preparation of recombinant human growth hormone.
Figure 14A:
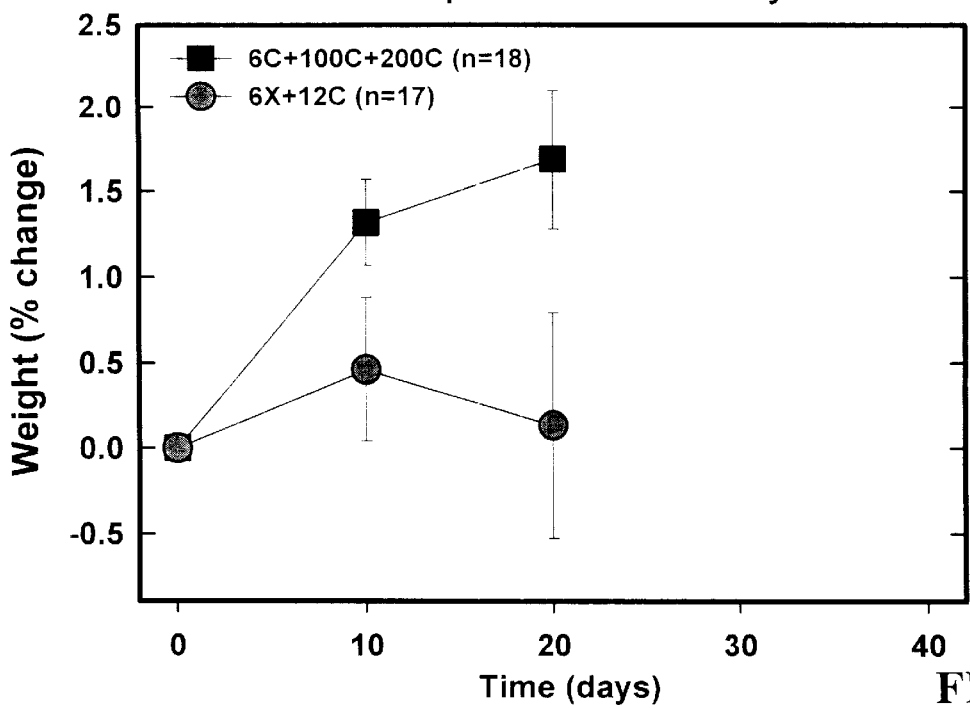
FIGS. 14A and 14B show the percentage weight change resulting from treatment using a 6 X+12 C potency and a 6 C+100 C+200 C potency homeopathic preparation of recombinant human growth hormone.
Figure 14B:
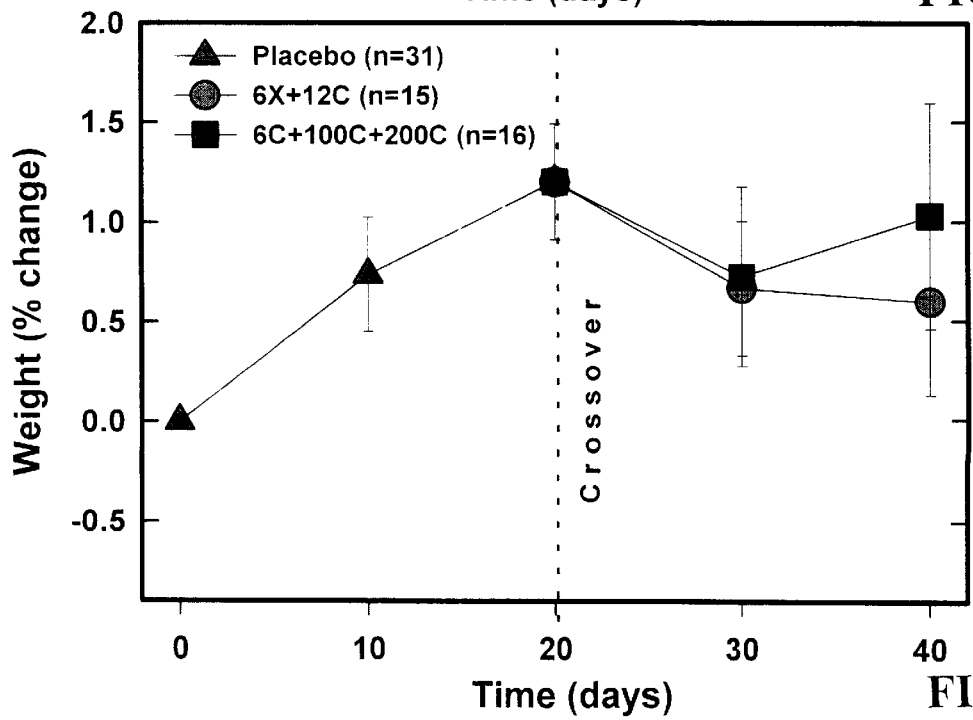

Measurements of hip and waist size were determined every ten days during the studies. FIG. 9A demonstrates that as early as 10 days following treatment of the high potency combination formulation, a decrease in hip size of 0.6 inches (+/−0.3 inches). This decrease was not sustained for the next ten days, and the placebo group also exhibited an increase during this same period. Ten days following cross-over from placebo, groups receiving high and low potency combinations had early decreases in hip size, −0.36 inches (+/−0.33 inches) and −0.51 inches (+/−0.65 inches), respectively. The treatment group receiving the high potency combination formulation sustained a minimal decrease until the end of the study (FIG. 9B). FIGS. 10A and 10B depict the change in waist size in adult males during the course of treatment with either high potency (solid squares) or low potency (solid triangles) HrhGH formulations. Treatment with the low potency HrhGH resulted in a gradual decrease in waist size over the 21-day period compared to the minimal decrease in waist size using the high potency formula or no substantial change on placebo (open circles). (FIG. 10a). Female subjects had varying responses to HrhGH over time (FIGS. 11A and 11B). In the first ten days of treatment with the low potency HrhGH (closed triangles), females rapidly decreased their waist size, but then gained it back, resulting in no net change in waist size after 21 days. In comparison, treatment with either form of the high potency formula for 21 days resulted in a decrease in waist measurements of approximately the same—0.8 inches. Interestingly, long-term treatment (42 days) with high potency formulations resulted in a sustained linear decrease in waist size in both men and women (FIG. 10A and FIG. 11A, solid diamonds). However, the effect was more pronounced in men than in women. In addition, chest size was shown to be significantly influenced by administration of HrhGH formulations as shown in FIGS. 12A and 12B. 1.4 Effects of Homeopathic Growth Hormone on Systolic Blood Pressure.

Systolic blood pressure was measured over the course of the studies. FIGS. 7A and 7B illustrate the change in systolic pressure over time for the treatment and placebo groups. Initial treatment with high and low potency combinations for 21 days resulted in no significant change in systolic pressure. Prolonged treatment over a 42 day period with high potency combination resulted in an 8% (+/−4%) decrease in systolic pressure (FIG. 7A). FIG. 7B demonstrates that following the placebo-treated group crossing over to the low potency combination formulation, the systolic pressure dropped by almost 10% after 21 days. The treatment group that crossed over to the high potency formulation for the same time period had no significant changes. Within the treatment group on the low potency combination formulation (n=13), there was a 4.5% (+/−2.9%) decrease in systolic blood pressure.

1.5 Determination of Potential Toxicity of Homeopathic hGH.

Figure 2A:
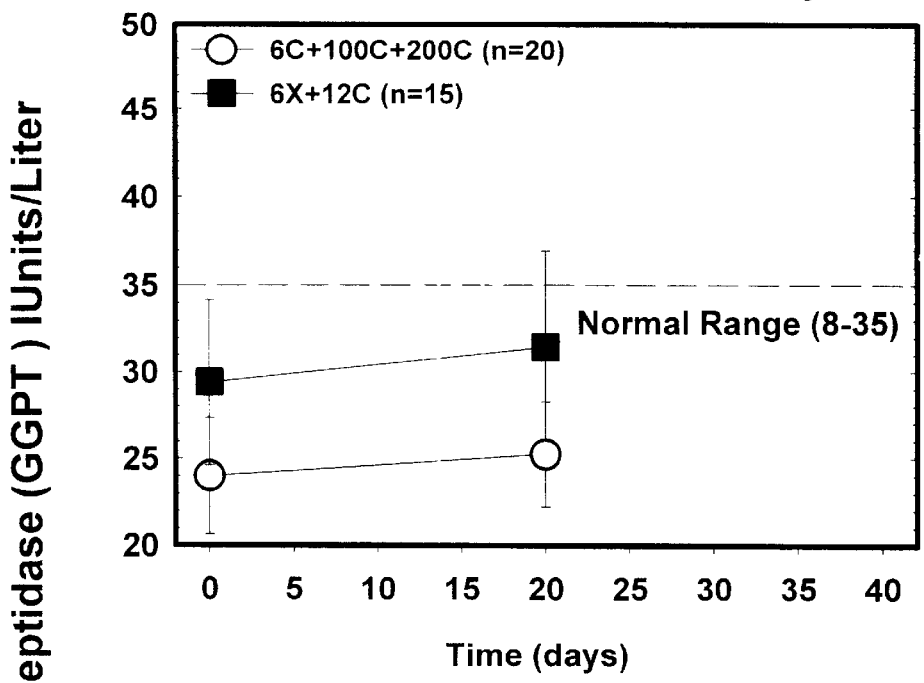
FIGS. 2A and 2B show the effect of treatment using a 6 X+12 C potency and a 6 C+100 C+200 C potency homeopathic preparation of recombinant human growth hormone (HrhGH) on the liver enzyme gamma-glutamyl transpeptidase (GGPT)
Figure 2B:
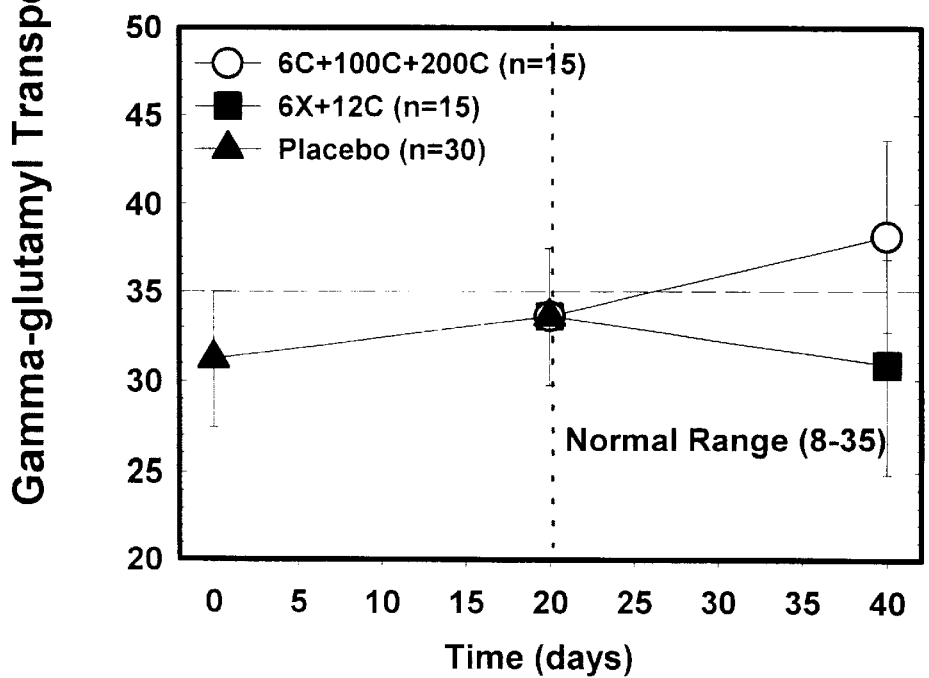
Figure 3A:
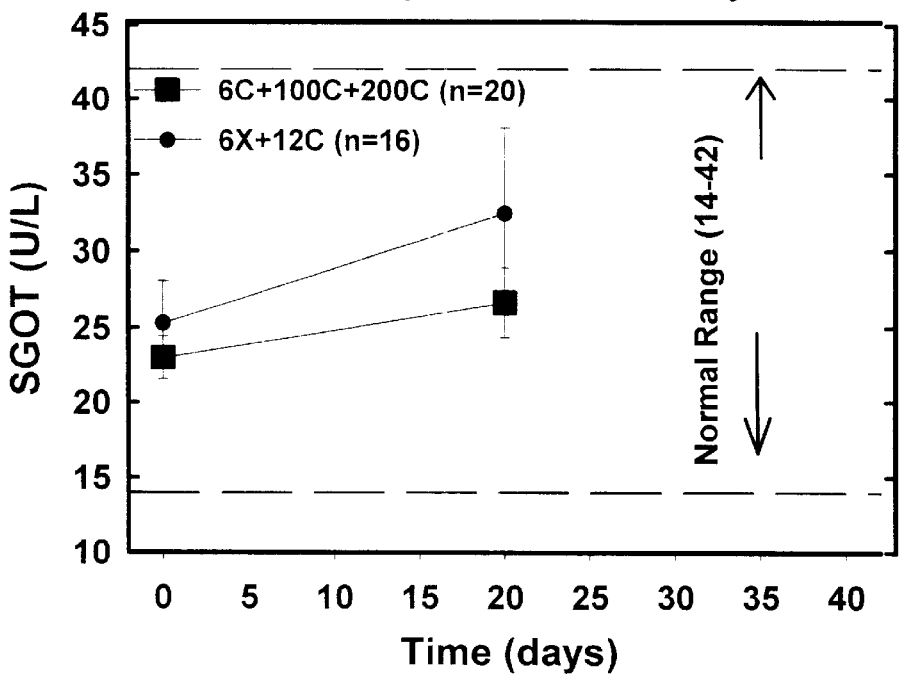
FIGS. 3A and 3B show the effect of treatment using a 6 X+12 C potency and a 6 C+100 C+200 C potency homeopathic preparation of recombinant human growth hormone on the liver enzyme aspartate aminotransferase (SGOT)
Figure 3B:
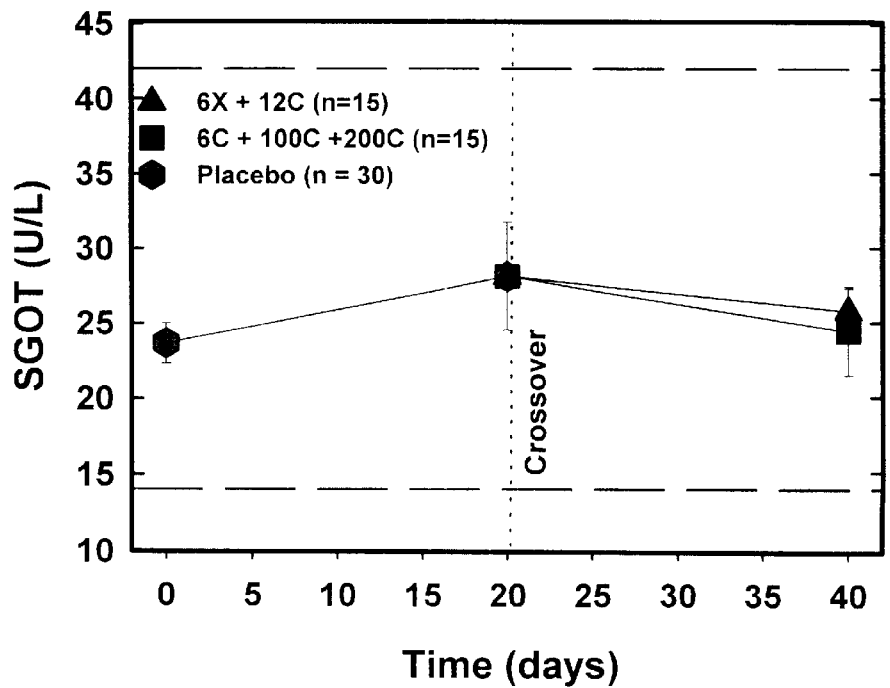
Figure 4A:
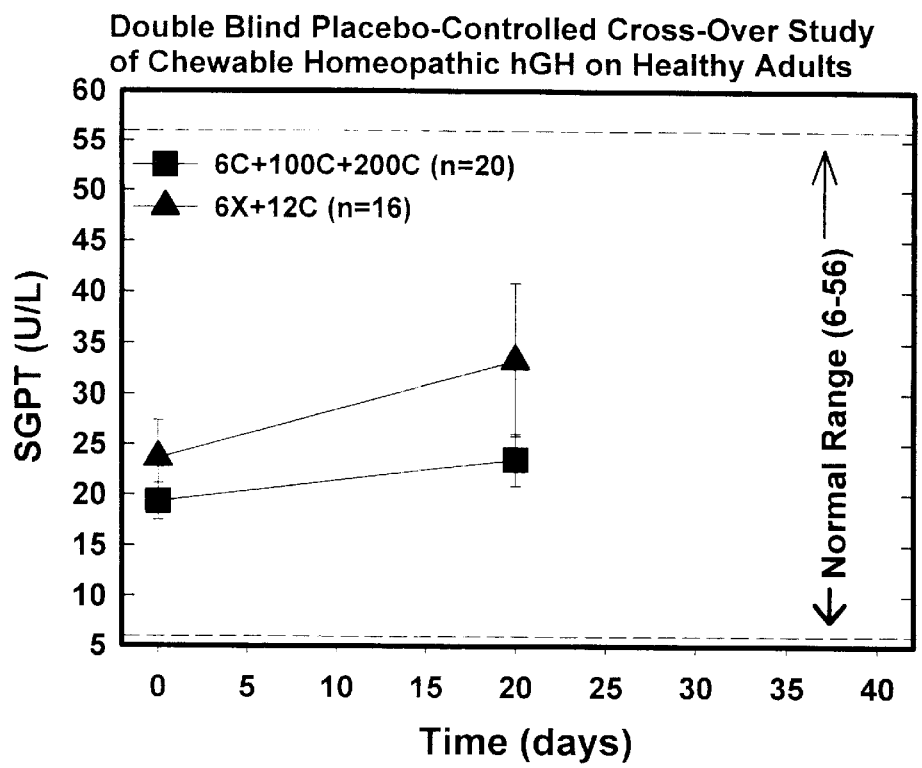
FIGS. 4A and 4B show the effect of treatment using a 6 X+12 C potency and a 6 C+100 C+200 C potency homeopathic preparation of recombinant human growth hormone on the liver enzyme alanine aminotransferase (SGPT)
Figure 4B:
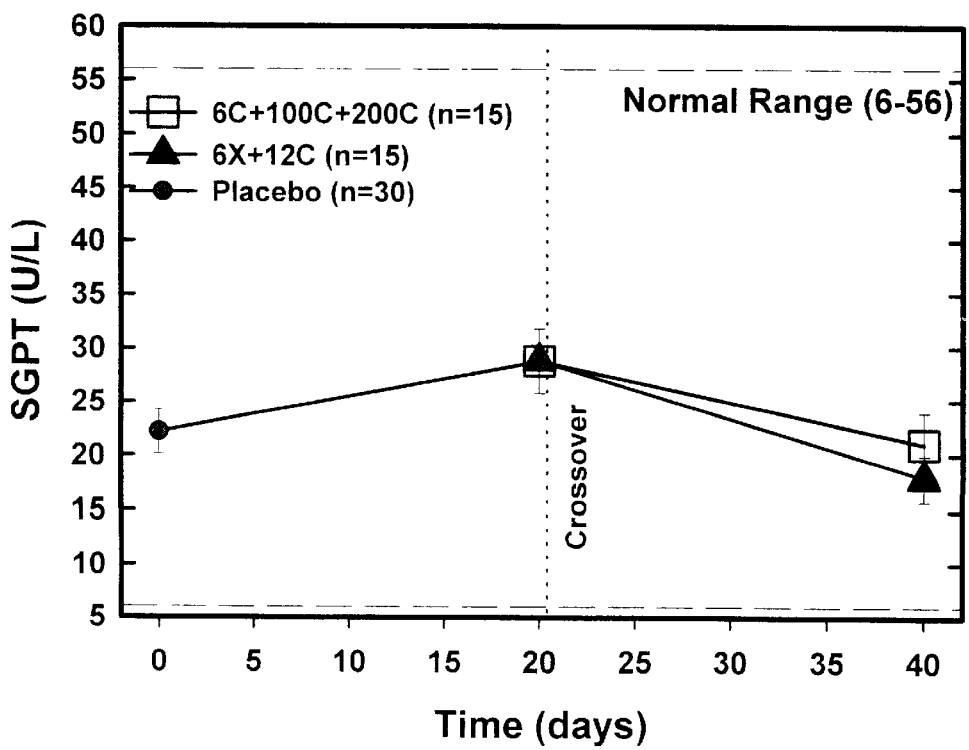
Figure 5A:
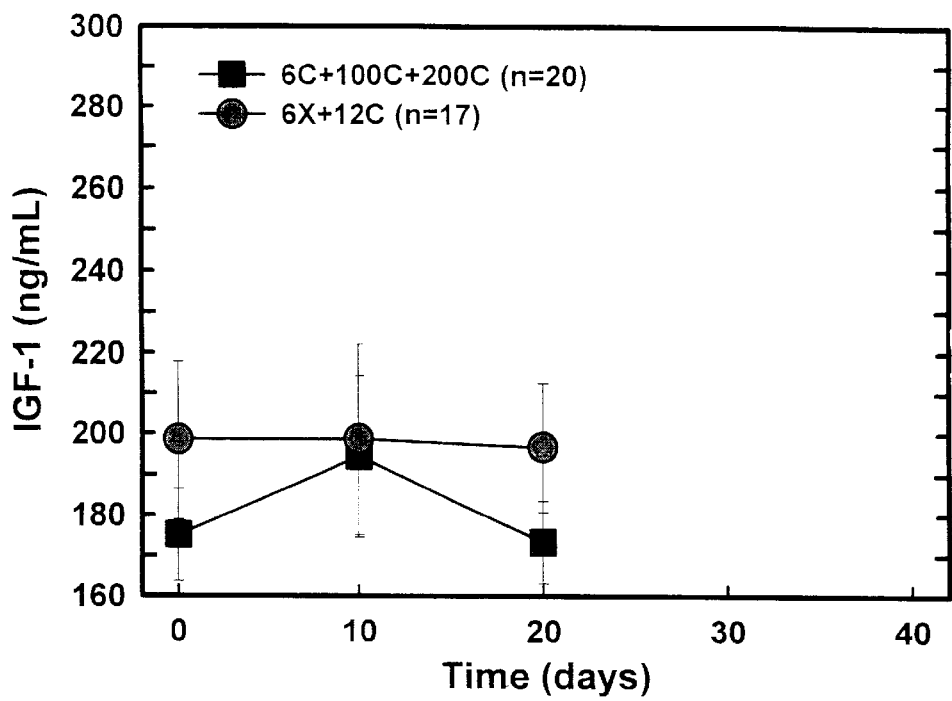
FIGS. 5A and 5B show the effect of treatment using a 6 X+12 C potency and a 6 C+100 C+200 C potency homeopathic preparation of recombinant human growth hormone on levels of $IGF_1$.
Figure 5B:
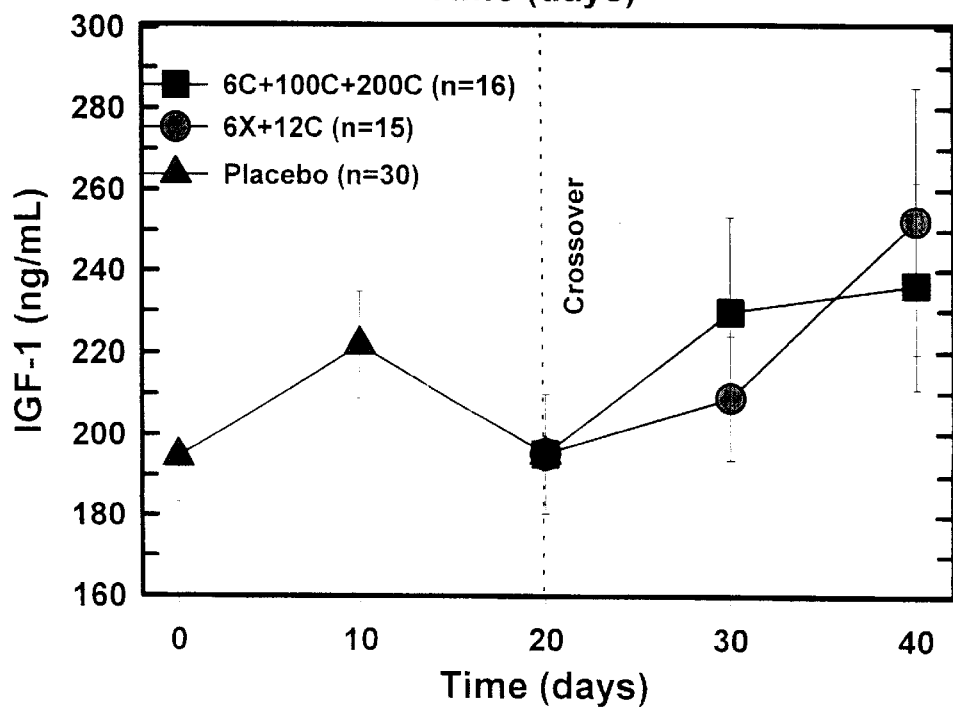

No significant changes in liver enzyme levels for GGPT, SGOT and SGPT, as described above, were detected over the course of the studies. SGOT and SGPT enzyme levels remained within the normal range in all treatment and placebo groups (FIGS. 3A, 3B and 4A, 4B). The average GGPT value for the treatment group that received placebo for the first three weeks, followed by a cross over to the 6 C formulation for an additional three weeks, was somewhat elevated, although not to a significant extent (FIGS. 2A and 2B). These results suggest the homeopathic formulations of the present invention are not toxic.

1.6 Effects of Homeopathic Growth Hormone on Self-Reporting Symptoms.

The primary self-reporting symptoms associated with age-related deficiency in human growth hormone is fatigue. In the Boulder Study, 38% of enrollees reported this symptom preceding treatment protocols. Additional symptoms generally recognized as being associated with hGH deficiency were reported by 21–31% of individuals prior to treatment, as shown in Table III, including abdominal obesity, loss of strength (also detected as decreased lean body mass), poor sleep, depression, and mood swings.

TABLE III

| | Potency | | | | | | | |
|---|---|---|---|---|---|---|---|---|
| | 6X + 12C | | 6C + 100C + 200C | | Placebo-CO | | Placebo Proving | |
| Symptom | Improve | Worsen | Improve | Worsen | Improve | Worsen | Improve | Worsen |
| CONSTITUTION | | | | | | | | |
| Fatigue | 70% | 10% | 69% | 30% | 58% | 42% | 36% | 41% |
| Weight Loss | 66% | 0% | 50% | 50% | 33% | 33% | 50% | 50% |
| SKIN & EXTREMITIES | | | | | | | | |
| Dry Scaly | 75% | 0% | 58% | 58% | 50% | 50% | 45% | 45% |
| Softness/Suppleness | 25% | 75% | 60% | 13% | 55% | 44% | 31% | 38% |
| EYE | | | | | | | | |
| Visual Changes | 50% | 25% | 82% | 9% | 50% | 38% | 73% | 27% |
| Floaters | 60% | 40% | 44% | 11% | 56% | 22% | 50% | 27% |
| ORAL | | | | | | | | |
| Bleeding Gums | 100% | 0% | 50% | 50% | 37% | 33% | 64% | |
| RESPIRATORY | | | | | | | | |
| Cough | 56% | 33% | 100% | 0% | 67% | 33% | 47% | 37% |
| Shortness of Breath | 75% | 25% | 100% | 0% | 50% | 50% | 40% | 50% |
| Phlegm | 50% | 50% | 71% | 29% | 25% | 50% | 55% | 33% |
| GASTROINTESTINAL-ABDOMINAL | | | | | | | | |
| Pain | 0% | 100% | 83% | 17% | 50% | 50% | 60% | 40% |
| Bloating | 67% | 0% | 80% | 20% | 25% | 50% | 25% | 25% |
| Abdominal Obesity | 50% | 50% | 73% | 18% | 63% | 38% | 40% | 40% |
| GENITO-URINARY | | | | | | | | |
| Discharge | 100% | 0% | 67% | 33% | 75% | 25% | 0% | 100% |
| Decreased Libido | 100% | 0% | 57% | 14% | 80% | 20% | 71% | 0% |
| Increased Libido | 100% | 0% | 60% | 40% | 83% | 17% | 38% | 50% |
| MUSCLO-SKELETAL | | | | | | | | |
| Imprvd. Phys. Appear. | 50% | 50% | 80% | 20% | 50% | 50% | 50% | 16% |
| Jaw Pain | 100% | 0% | 80% | 20% | 67% | 33% | 75% | 25% |
| Knee Pain | 64% | 27% | 80% | 10% | 89% | 11% | 46% | 31% |
| Joint Pain | 44% | 22% | 72% | 11% | 87% | 7% | 45% | 18% |

TABLE III-continued

| | Potency | | | | | | | |
|---|---|---|---|---|---|---|---|---|
| | 6X + 12C | | 6C + 100C + 200C | | Placebo-CO | | Placebo Proving | |
| Symptom | Improve | Worsen | Improve | Worsen | Improve | Worsen | Improve | Worsen |
| PSYCHOLOGICAL | | | | | | | | |
| Apathy | 100% | 0% | 80% | 20% | 50% | 25% | 66% | 22% |
| Anxiety | 83% | 17% | 60% | 0% | 63% | 25% | 50% | 18% |
| Anger | | | 83% | 0% | 67% | 0% | 59% | 35% |
| Poor Quality of Sleep | 57% | 29% | 45% | 35% | 38% | 38% | 44% | 24% |
| NEUROLOGICAL | | | | | | | | |
| Headaches | 64% | 36% | 69% | 31% | 60% | 40% | 50% | 36% |
| Arms/Legs Weakness | 40% | 10% | 100% | 0% | 60% | 40% | 66% | 33% |
| Joint Swelling | 100% | 100% | 100% | 0% | 100% | 0% | 50% | 0% |
| Knee Swelling | 100% | 0% | 100% | 0% | 100% | 0% | 66% | 0% |
| Back Pain | 67% | 17% | 71% | 14% | 82% | 0% | 55% | 37% |
| | | | PLACEBO EFFECTS | | | | | |
| CONSTITUTION | | | | | | | | |
| Night Sweats | 60% | 40% | 80% | 20% | 25% | 50% | 80% | 20% |
| Vitality | 66% | 33% | 30% | 45% | 60% | 30% | 35% | 41% |
| SKIN & EXTREMITIES | | | | | | | | |
| Rash | 33% | 67% | 67% | 17% | 100% | 0% | 66% | 33% |
| Itches | 50% | 0% | 22% | 56% | 67% | 33% | 66% | 25% |
| Skin Radiance | 33% | 67% | 50% | 30% | 71% | 29% | 45% | 45% |
| Thickness | 50% | 50% | 100% | 0% | 100% | 0% | 60% | 30% |
| Wrinkles | 64% | 0% | 80% | 7% | 85% | 15% | 38% | 28% |
| Hemorrhoids | 80% | 0% | 42% | 8% | 80% | 20% | — | — |
| RESPIRATORY | | | | | | | | |
| Nasal Congestion | 33% | 67% | 38% | 46% | 89% | 11% | 42% | 31% |
| Sinus Congestion | 64% | 36% | 55% | 28% | 67% | 33% | 50% | 39% |
| GASTROINTESTINAL -ABDOMINAL | | | | | | | | |
| Constipation | 80% | 20% | 43% | 29% | 86% | 14% | 55% | 45% |
| Reduced Appetite | 100% | 0% | 60% | 40% | 100% | 0% | 20% | 66% |
| Increased Appetite | 50% | 50% | 86% | 14% | 83% | 17% | 55% | 33% |
| Sugar Cravings | 88% | 13% | 89% | 11% | 89% | 11% | 41% | 32% |
| MUSCLO-SKELETAL | | | | | | | | |
| Joint Pain | 44% | 22% | 72% | 11% | 87% | 7% | 45% | 18% |
| Muscle Pain | 0% | 100% | 58% | 33% | 83% | 17% | 45% | 30% |
| Muscle Wasting | 67% | 33% | 67% | 0% | 100% | 0% | 0% | — |
| Incr. Physical Strength | 67% | 33% | 70% | 20% | 80% | 20% | 46% | 40% |
| Dec. Physical Strength | (60) 67% | (40)33% | 90% | 0% | 83% | 17% | 54% | 38% |
| Enhcd. Phys. Endrnce. | 60% | 40% | 82% | 9% | 100% | 0% | 35% | 41% |
| Faster Workout Recvry | 50% | 50% | 67% | 22% | 66% | 0% | 55% | 22% |
| Knee Pain | 64% | 27% | 80% | 10% | 89% | 11% | 46% | 31% |
| PSYCHOLOGICAL | | | | | | | | |
| Mood Swings | 71% | 29% | 80% | 10% | 88% | 13% | 33% | 29% |
| Increased Energy | | 36% | 55% | 100% | 0% | 53% | 32% | |
| Depression | 60% | 10% | 69% | 22% | 56% | 11% | 65% | 30% |
| Morning Tiredness | 55% | 27% | 48% | 35% | 67% | 33% | 49% | 20% |
| Night Awakenings | 67% | 22% | 67% | 0% | 73% | 27% | 41% | 23% |
| Poor Depth of Sleep | 38% | 50% | 44% | 25% | 43% | 43% | 55% | 33% |
| Poor Length of Sleep | 43% | 57% | 10% | 60% | 33% | 33% | 50% | 25% |
| NEUROLOGICAL | | | | | | | | |
| Poor Short Term Memory | 63% | 38% | 33% | 44% | 90% | 10% | 57% | 36% |
| Tingling/Burning Sensation | 100% | 0% | 100% | 0% | 100% | 0% | 25% | 50% |
| OTHER | | | | | | | | |
| Ears Ringing | 17% | 67% | 29% | 36% | 60% | 20% | 50% | 30% |
| Discomfort Between Shoulder Blades | 50% | 33% | 71% | 14% | 83% | 17% | 50% | 50% |
| Muscle Weakness | 37% | 37% | 67% | 33% | 83% | 17% | 100% | — |
| Difficulty | 100% | 0% | 100% | 0% | 100% | 0% | 0 | 100% |

TABLE III-continued

| | Potency | | | | | | | |
| --- | --- | --- | --- | --- | --- | --- | --- | --- |
| | 6X + 12C | | 6C + 100C + 200C | | Placebo-CO | | Placebo Proving | |
| Symptom | Improve | Worsen | Improve | Worsen | Improve | Worsen | Improve | Worsen |
| Breathing/Air Hunger | | | | | | | | |
| Joint Swelling | 100% | 100% | 100% | 0% | 100% | 0% | 50% | 0% |
| Knee Swelling | 100% | 0% | 100% | 0% | 100% | 0% | 66% | 0% |
| Back Pain | 67% | 17% | 71% | 14% | 82% | 0% | 55% | 37% |
| Carpal Tunnel | 0% | 0% | 100% | 0% | 100% | 0% | 100% | 0% |
| Hair Color | 67% | 33% | 67% | 33% | 100% | 0% | 100% | 0% |

Although the present invention has been described in terms of specific embodiments, changes and modifications can be carried out without departing from the scope of the invention which is intended to be limited only by the scope of the appended claims.

What is claimed is:

1. A composition comprising a homeopathic preparation of purified growth hormone wherein the concentration of said purified growth hormone is between about $1\times10^{-6}$ molar and about $1\times10^{-100,000}$ molar.

2. A composition as recited in claim 1 additionally comprising at least one component selected from the group consisting of: a growth factor, a vitamin, a mineral, an amino acid and traditional homeopathics.

3. A composition as recited in claim 1 wherein the composition is a liquid.

4. A composition as recited in claim 1 wherein the composition is impregnated on a solid medium.

5. A composition as recited in claim 4 wherein said solid medium is a tablet.

6. A method for modulating IGF-1 levels in serum of a patient comprising administering an effective amount of the composition of claim 1 to said patient.

7. A method for modulating lean body mass of a patient comprising administering an effective amount of the composition of claim 1 to said patient.

8. A composition comprising a purified growth hormone having a homeopathic potency selected from the group consisting of 6 C, 12 C, 30 C, 100 C, 200 C and 1M (1000 C).

9. A composition comprising a purified growth hormone having a homeopathic potency of 200 C.

10. A composition comprising a purified growth hormone having a homeopathic potency of 6 C.

11. A composition comprising a purified growth hormone having a homeopathic potency of 100 C.

12. A composition comprising a purified growth hormone in a combination potency formulation having at least two homeopathic potencies.

13. A composition as recited in claim 12, wherein the combination potency formulation comprises 6 X and 12 C homeopathic potencies.

14. A composition as recited in claim 12 wherein the combination potency formulation comprises 6 C, 100 C and 200 C homeopathic potencies.

15. A composition as recited in any of claims 1, 9, 10 or 11, wherein the purifier growth hormone is at least 95% pure.

16. A composition as recited in any of claims 1, 9, 10 or 11, wherein the purified growth hormone is recombinant human growth hormone.

17. A composition as recited in any of claims 1, 9, 10 and 11, wherein the purified growth hormone is recombinant human growth hormone having a biological specific activity of approximately 2.6 Units/mg based on the World Health Organization reference standard.

18. A composition as recited in claim 1 wherein the composition is formulated in a lotion for topical application.

19. A composition comprising purified growth hormone at a homeopathic potency selected from the group consisting of: 15 X, 20 X, 24 X and 800 X.

* * * * *